US008821856B2

(12) United States Patent
Baltimore et al.

(10) Patent No.: US 8,821,856 B2
(45) Date of Patent: Sep. 2, 2014

(54) METHOD OF TARGETED GENE DELIVERY USING VIRAL VECTORS

(75) Inventors: David Baltimore, Pasadena, CA (US); Pin Wang, Pasadena, CA (US); Lili Yang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 100 days.

(21) Appl. No.: 13/041,115

(22) Filed: Mar. 4, 2011

(65) Prior Publication Data
US 2011/0212530 A1    Sep. 1, 2011

Related U.S. Application Data

(63) Continuation of application No. 11/446,353, filed on Jun. 1, 2006, now abandoned.

(60) Provisional application No. 60/686,215, filed on Jun. 1, 2005, provisional application No. 60/738,078, filed on Nov. 19, 2005.

(51) Int. Cl.
*C12N 15/867* (2006.01)
*C07K 16/28* (2006.01)
*C07K 17/02* (2006.01)
*A61K 35/76* (2006.01)
*C07K 14/155* (2006.01)

(52) U.S. Cl.
USPC .............. 424/93.6; 424/178.1; 424/152.1; 424/199.1; 424/207.1; 530/388.2; 530/387.3; 530/395; 435/235.1; 435/69.3; 435/7.1; 435/372

(58) Field of Classification Search
CPC ............. A61K 47/48561; A61K 2039/5256; C12N 2740/15045; C12N 2810/859; C12N 2740/10045; C12N 15/867; C07K 14/1808; C07K 2317/62; C07K 2317/64
See application file for complete search history.

(56) References Cited

U.S. PATENT DOCUMENTS

| 5,168,062 A | 12/1992 | Stinski |
| 5,298,420 A | 3/1994 | Chang |
| 5,385,839 A | 1/1995 | Stinski |
| 6,013,516 A | 1/2000 | Verma et al. |
| 6,017,761 A | 1/2000 | Rigg et al. |
| 6,140,114 A | 10/2000 | Klatzmann et al. |
| 6,218,181 B1 | 4/2001 | Verma et al. |
| 6,297,004 B1* | 10/2001 | Russell et al. ............ 435/5 |
| 6,306,401 B1 | 10/2001 | Brown et al. |
| 6,416,997 B1 | 7/2002 | Mir-Shekari et al. |
| 6,432,699 B1 | 8/2002 | Meruelo et al. |
| 6,531,123 B1 | 3/2003 | Chang |
| 6,534,064 B1 | 3/2003 | O'Hagan et al. |
| 6,627,442 B1 | 9/2003 | Humeau et al. |
| 6,830,892 B2 | 12/2004 | Marasco et al. |
| 7,033,834 B2 | 4/2006 | Valerio et al. |
| 7,090,837 B2 | 8/2006 | Spencer et al. |
| 7,195,916 B2 | 3/2007 | Qin et al. |
| 7,285,642 B2 | 10/2007 | Figdor et al. |
| 7,323,619 B2 | 1/2008 | Baltimore et al. |
| 7,429,481 B2 | 9/2008 | Bergman et al. |
| 7,455,833 B2 | 11/2008 | Thorpe et al. |
| 7,604,802 B2 | 10/2009 | O'Hagan et al. |
| 7,611,712 B2 | 11/2009 | Karp |
| 7,612,173 B2 | 11/2009 | Abrecht et al. |
| 7,638,133 B2 | 12/2009 | Honda et al. |
| 7,771,979 B2 | 8/2010 | Polo et al. |
| 2002/0155430 A1 | 10/2002 | Marsco et al. |
| 2003/0059944 A1 | 3/2003 | Lois-Caballe et al. |
| 2003/0068821 A1 | 4/2003 | Lois-Caballe et al. |
| 2003/0101471 A1 | 5/2003 | Baltimore et al. |
| 2003/0129163 A1 | 7/2003 | Hall et al. |
| 2003/0207438 A1* | 11/2003 | Schauber et al. .......... 435/235.1 |
| 2004/0071661 A1* | 4/2004 | Klatzmann et al. .......... 424/93.2 |
| 2004/0091853 A1 | 5/2004 | Hazuda et al. |
| 2005/0003547 A1 | 1/2005 | Spencer et al. |
| 2007/0275873 A1 | 11/2007 | Heidner et al. |
| 2008/0003682 A1 | 1/2008 | Lois-Caballe et al. |
| 2008/0019998 A1 | 1/2008 | Wang et al. |

(Continued)

FOREIGN PATENT DOCUMENTS

| WO | WO-96/17072 | 6/1996 |
| WO | WO-00/09730 | 2/2000 |

(Continued)

OTHER PUBLICATIONS

Morizono et al, Antibody-Directed Targeting of Retroviral Vectors via Cell Surface Antigens, Journal of Virology, Sep. 2001, p. 8016-8020 vol. 75, No. 17.*
van Brockhoven, Targeting Dendritic Cells with Antigen-Containing Liposomes: A Highly Effective Procedure for Induction of Antitumor Immunity and for Tumor Immunotherapy, Cancer Research 64, 4357-4365, Jun. 15, 2004.*
Ageichik et al., Lentivector trargeting to dendritic cells. *Molec. Ther.*, 16(6): 1008-09 (2008).
Analyses of Merck's HIV vaccine Step' study. The Medical News, Nov. 12, 2008, Accessed at http://www.new-medical.net/news/2008/11/12/42892.aspx on Nov. 20, 2009.

(Continued)

*Primary Examiner* — Maria Marvich
(74) *Attorney, Agent, or Firm* — Marshall, Gerstein & Borun LLP

(57) ABSTRACT

Methods and compositions are provided for delivering a polynucleotide encoding a gene of interest to a target cell using a virus. The virus envelope comprises a cell-specific binding determinant that recognizes and binds to a component on the target cell surface, leading to endocytosis of the virus. A separate fusogenic molecule is also present on the envelope and facilitates delivery of the polynucleotide across the membrane and into the cytosol of the target cell. The methods and related compositions can be used for treating patients having suffering from a wide range of conditions, including infection, such as HIV; cancers, such as non-Hodgkin's lymphoma and breast cancer; and hematological disorders, such as severe combined immunodeficiency.

12 Claims, 17 Drawing Sheets

(56) References Cited

U.S. PATENT DOCUMENTS

| | | | |
|---|---|---|---|
| 2008/0134352 A1 | 6/2008 | Baltimore et al. | |
| 2008/0227736 A1 | 9/2008 | Chen et al. | |
| 2010/0184206 A1 | 7/2010 | Chen et al. | |

FOREIGN PATENT DOCUMENTS

| | | |
|---|---|---|
| WO | WO-00/61772 | 10/2000 |
| WO | WO-01/16342 | 3/2001 |
| WO | WO-2004/056966 | 7/2004 |
| WO | WO-2004/067710 | 8/2004 |
| WO | WO-2005/118802 | 12/2005 |
| WO | WO-2006/130855 | 12/2006 |
| WO | WO-2008/011636 | 1/2008 |
| WO | WO-2009/076524 | 6/2009 |

OTHER PUBLICATIONS

Apolonia et al., Stable Gene Transfer to Muscle Using Non-integrating Lentiviral Vectors, Molecular Therapy 15:1947-1954, 2007.
Bailey et al., Transmission of human immunodeficiency virus type 1 from a patient who developed AIDS to an elite suppressor, *J. Virol.*, 82(15): 7395-410 (2008).
Banchereau et al., Dendritic cells and the control of immunity, *Nature*, 392: 245-52 (1998).
Banchereau et al., Dendritic cells as therapeutic vaccines against cancer, *Nat. Rev. Immunol.*, 5: 296-306 (2005).
Bangham et al., What is required of an HIV vaccine? *Lancet*, 350: 1617-21 (1997).
Barouch et al., Adenovirus vector-based vaccines for human immunodeficiency virus type 1, *Hum. Gene. Ther.*, 16: 149-56 (2005).
Barouch et al., Challenges in the development of an HIV-1 vaccine, *Nat. Rev.*, 455: 613-9 (2008).
Bayer et al., A Large U3 Deletion Causes Increased In Vivo Expression From a Nonintegrating Lentiviral Vector, Molecular Therapy 16:1968-1976, 2008.
Bear et al., Heparin-binding and patterns of virulence for two recombinant strains of Sindbis virus, Virology 347:183-190, 2006.
Belousova et al., Genetically targeted adenovirus vector directed to CD40-expressing cells, *J. Virol.*, 77: 11367-77 (2003).
Bhardwaj et al., Interactions of viruses with dendritic cells: A double-edged sword. *J. Exp. Med.*, 186(6): 795-9 (1997).
Bonifaz et al., Efficient targeting of protein antigen to the dendritic cell receptor DEC-205 in the steady state leads to antigen presentation on major histocompatibility complex class I products and peripheral CD8+ T cell tolerance, *J. Exp. Med.*, 196: 1627-38 (2002).
Bonifaz et al., In vivo targeting of antigens to maturing dendritic cells cia the DEC-205 receptor improves T cell vaccination, *J. Exp. Med.*, 199(6): 815-24 (2004).
Branch, A good antisense molecule is hard to find, *TIBS*, 23: 45-50 (1998).
Breckpot et al., Lentiviral vectors for cancer immunotherapy: transforming infectious particles into therapeutics, Gene Therapy 14:847-862, 2007.
Burgers et al., The challenges of HIV vaccine development and testing, *Best Practice & Research: Clininal Obstetrics & Gynaecology*, 19(1): 277-91 (2005).
Butler et al., A quantitative assay for HIV DNA integration in vivo. *Nat. Med.*, 7: 631-4 (2001).
Byrnes et al., Binding of Sindbis virus to cell surface heparan sulfate. *J. Virol.*, 72: 7349-56 (1998).
Case et al., Stable transduction of quiescent CD34+CD38- human hematopoietic cells by HIV-1-based lentiviral vectors, *Proc. Natl. Acad. Sci. USA*, 96(6): 2988-93 (1999).
Chandrashekran et al., Targeted retroviral transduction of c-kit(+) hematopoietic cells using novel ligand display technology, *Blood*, 104: 2697-703 (2004).
Cheng et al., Mechanism of ad5 vaccine immunity and toxicity: Fiber shart targeting of dendritic cells. *PLoS Pathog.*, 3:e25 (2007).
Cheong et al., Improved cellular and humoral immune responses in vivo following targeting of HIV Gag to dendritic cells within human anti-human DEC205 monoclonal antibody. *Blood*, 116: 3828-38 (2010).
Chirila et al., The use of synthetic polymers for delivery of therapeutic antisense oligodeoxynucleotides, *Biomaterials*, 23: 321-42 (2002).
Choi et al., Hybrid HIV/MSCV LTR enhances transgene expression of lentiviral vector in human CD34+ hematopoietic cells, *Stem Cells*, 19: 236-46 (2001).
Chou et al., Expression of chimeric monomer and dimer proteins on the plasma membrane of mammalian cells, *Biotechnol. Bioengin.*, 65(2): 160-9 (1999).
Chu et al., Retroviral vector particles displaying the antigen-binding site of an antibody enable cell-type-specific gene transfer, *J. Virol.*, 69(4): 2659-63 (1995).
Cockrell et al., Gene delivery by lentivirus vectors, Mol. Biotechnol. 36:184-204, 2007.
Cohen, Is an effective HIV vaccine feasible? *Science*, 309: 99 (2005).
Collins et al., Gene therapy meets vaccine development. *TRENDS Biotech.*, 22(12): 623-6 (2004).
Cosset et al., Retroviral retargeting by envelopes expressing an N-terminal binding domain, *J. Virol.*, 69(10): 6314-22 (1995).
Coutant et al., Protective Antiviral Immunity Conferred by a Nonintegrative Lentiviral Vector-Based Vaccine, Plos ONE 3:e3973:1-6, 2008.
Cronin et al., Altering the tropism of lentiviral vectors through pseudotyping. *Curr. Gene Ther.*, 5(4): 387-98 (2005).
Dai et al., HIV-I Gag-specific immunity induced by a lentivector-based vaccine directed to dendritic cells, Proc. Natl. Acad. Sci. U. S. A. 106:20382-20387, 2009.
Dakappagari et al., Internalizing antibodies to the C-type lectins, L-SIGN and DC-SIGN, inhibit viral glycoprotein binding and deliver antigen to human dendritic cells for the induction of T cell responses. *J. Immunol.*, 176: 426-40 (2006).
De Felipe et al., Skipping the co-expression problem: The new 2A CHYSEL technology, *Genet. Vaccines Ther.*,2(13): 1-6 (2004).
De Filipe et al., Targeting of proteins derived from self-processing polyproteins containing multiple signal sequences, *Traffic*, 5: 616-26 (2004).
De Gruijl et al., Prolonged maturation and enhanced transduction of dendritic cells migrated from human skin explants after in situ delivery of CD40-targeted adenoviral. *J. Immunol.*, 169: 5322-533 (2002).
De Ines et al., Apoptosis of a human melanoma cell line specifically induced by membrane-bound single-chain antibodies, *J. Immunol.*, 163: 3948-56 (1999).
Dimitrov et al., Quantitation of human immunodeficiency virus type 1 infection kinetics. *J. Virol.*, 67(4): 2182-90 (1993).
Dimitrov et al., Virus entry: Molecular mechanisms and biomedical applications, *Nat. Rev. Microbiol.*, 2: 109-22 (2004).
Dong et al., HIV-specific cytotoxic T cells from long-term survivors select a unique T cell receptor. *J. Exp. Med.* 200(12): 1547-57 (2004).
Drose et al., Bafilomycins and concanamycins as inhibitors of V-ATPases and P-ATPases, *J. Exp. Biol.*, 200: 1-8 (1997).
Dullaers et al., Induction of effective therapeutic antitumor immunity by direct in vivo administration of lentiviral vectors. *Gene Ther.*, 13: 630-40 (2006).
Engelmayer et al., Vaccinia virus inhibits the maturation of human dendritic cells: A novel mechanism of immune evasion. *J. Immunol.*, 163: 6762-8 (1999).
Engering et al., Subset of DC-SIGN dendritic cells in human blood transmits HIV-1 to T lymphocytes, Blood 100(5):1780-1786, 2002.
Esslinger et al., Efficient transduction of dendritic cells and induction of a T-cell response by third-generation lentivectors, *Hum. Gene Ther.*, 13: 1091-100 (2002).
Esslinger et al., In vivo administration of a lentiviral vaccine targets DCs and induces efficient CD8(+) T cell responses. *J. Clin. Invest.*, 111: 1673-81 (2003).
Evans et al., Human cord blood CD34+CD38- cell transduction via lentivirus-based gene transfer ventors, *Hum. Gene Ther.*, 10(9): 1479-89 (1999).

(56) References Cited

OTHER PUBLICATIONS

Fielding et al., Inverse targeting of retroviral ventors: Selective gene transfer in a mixed population of hematopoietic and nonhematopoietic cells, *Blood*, 91(5): 1802-9 (1998).

Figdor et al., Dendritic cell immunotherapy: Mapping the way. *Nat. Med.*, 10: 475-80 (2004).

Frolov et al., Translation of Sindbis virus mRNA: analysis of sequences downstream of the iniating AUG codon that enhances translation. *J. Virol.*, 70(2): 1182-90 (1996).

Gardner et al., Infection of Human Dendritic Cells by a Sindbis Virus Replicon Vector is Determined by a Single Amino Acid Substitution in the E2 Glycoprotein, J. Virol. 74:11849-11857, 2000.

Geijtenbeek et al., Self- and Nonself-Recognition by C-Type Lectins on Dendritic Cells, Annu. Rev. Immunol. 22:33-54, 2004.

Geijtenbeek et al., DC-SIGN, a dendritic cell-specific HIV-1-binding protein that enhances trans-infection of T cells, *Cell*, 100: 587-97 (2000).

Geijtenbeek et al., Identification of DC-SIGN, a novel dendritic cell-specific ICAM-3 receptor that supports primary immune responses. *Cell*, 100: 575-85 (2000).

Gollan et al., Redirecting retroviral tropism by insertion of short, nondisruptive peptide ligands into envelope, *J. Virol.*, 76(7): 3558-63 (2002).

Gong et al., Induction of antigen-specific antitumor immunity with adenovirus-transduced dendritic cells, *Gene Ther.*, 4: 1023-8 (1997).

Granelli-Piperno et al., Dendritic cells, infected with vesicular stromatitis virus-pseudotyped HIV-1, present viral antigens to CD4+ and CD8+ T cells from HIV-1-infected individuals.*J. Immunol.*, 165: 6620-6 (2000).

Gunning et al., A human beta-actin expression vector system directs high-level accumulation of antisense transcripts, *Proc. Natl. Acad. Sci. USA*, 84: 4831-6 (1987).

Gupta et al., Antibody responses against HIV in *Rhesus macaques* following combinations of mucosal and systemic immunizations with chimeric alphavirus-based replicon particles, *AIDS Res., Hum. Retroviruses*, 22(10): 993-7 (2006).

Han et al., Ligand-directed retroviral targeting of human breast cancer cells, *Proc. Natl. Acad. Sci. USA*, 92: 9747-51 (1995).

Hanke et al., Pre-clinical development of a multi-CTL epitope-based DNA prime MVA boost vaccine for AIDS. *Immunol. Lett.*, 66: 177-81 (1999).

Hatziioannou et al., Incorporation of fowl plague virus hemagglutinin in murine leukenia virus particles and analysis of the infectivity of the pseudotyped retroviruses, *J. Virol.*, 72: 5313 (1998).

Iwakuma et al., Self-activating lentiviral ventors with U3 and U5 modifications, *Virology*, 261: 120-32 (1999).

Iwasaki et al., Regulation of adaptive immunity by the innate immune system. *Science*, 327: 291-5 (2010).

Jahn et al., Analysing c-kit internalization using a functional c-kit-EGFP chimera containing the fluorochrome within the extracellular domain, *Oncogene*, 21: 4508-20 (2002).

Jiang et al., Cell-type-specific gene transfer into human cells with retroviral vectors that display single-chain antibodies, *J. Virol.*, 72(12): 10148-56 (1998).

Kahl et al., Human immunodeficiency virus type 1—derived lentivirus vectors pseudotyped with envelope glycoproteins derived from Ross River virus and Semliki Forest virus. *J. Virol.*, 79(3): 1421-30 (2004).

Kahl et al., Lentiviral vectors pseudotyped with glycoproteins from Ross River and vesicular stomatitis viruses: Variable transduction related to cell type and culture conditions. *Molec. Ther.*, 11(3): 470-82 (2005).

Kamrud et al., Analysis of Venezuelan equine encephalitis replicon particles packages in different coats. PLoS ONE, 3(7): e2709 (2008).

Kaplan et al., Induction of antitumor immunity with dendritic cells transduced with adenvirus vector-encoding edogenous tumor-associated antigens, *J. Immunol.*, 163: 699-707 (1999).

Karasuyama et al., Autocrine growth and tumorigenicity of interleukin 2-dependent helper T cells transfected with IL-2 gene, *J. Exp. Med.*, 169: 13-25 (1989).

Keller et al., Overexpression of HOX11 leads to the immortalization of embryonic presursors with both primitive and definitive hematopoietic potential, *Blood*, 92(3): 877-87 (1998).

Kielian et al., Alphavims Entry and Membrane Fusion, Viruses 2:796-825, 2010.

Kim et al., Induction of therapeutic antitumor immunity by in vivo administration of a lentiviral vaccine. *Hum. Gene Ther.*, 16: 1255-66 (2005).

Kirk et al., Gene-modified dendritic cells for use in tumor vaccines. *Hum. Gene Ther.*, 11: 797-803 (2000).

Klimstra et al., Adaptation of Sindbis Virus to BHK Cells Selects for Use of Heparan Sulfate as an Attachment Receptor, J. Virol. 72:7357-7366, 1998.

Klimstra et al., DC-SIGN and L-SIGN Can Act as Attachment Receptors for Alphaviruses and Distinguish between Mosquito Cell- and Mammalian Cell-Derived Viruses,.I. Virol. 77:12022-12032, 2003.

Klimstra et al., The Furin Protease Cleavage Recognition Sequence of Sindbis Virus PE2 Can Mediate Virion Attachment to Cell Surface Heparan Sulfate, J. Virol. 73:6299-6306, 1999.

Kolokoltsov et al., Efficient functional pseudotyping of oncoretroviral and lentiviral vectors by Venezuelan equine encephalitis virus envelope proteins. *J. Virol.*, 79(2): 756-63 (2005).

Korst et al., Active, specific immunotherapy for lung cancer: hurdles and strategies using genetic modification. *Annu. Thor. Surg.*, 76: 1319-26 (2003).

Korth et al., Interferon inhibits the replication of HIV-1, SIV, and SHIV chimeric viruses by distinct mechanisms. *Virology*, 247: 265-73 (1998).

Kung et al., A murine leukimia virus (MuLV) long terminal repeat derived from *Rhesus macaques* in the context of a lentivirus vector and MuLV gag sequence results in high-level gene expression in human T lymphocytes, *J. ViroL*, 74(8): 3668-81 (2000).

Kwon et al., Determination of infectious retrovirus concentration from colony-forming assay with quantitative analysis. J. Virol., 77(10): 5712-20 (2003).

Lavillette et al., Retargeting gene delivery using surface-engineered retroviral vetor particles, *Curr. Opin. Biotech.*, 12: 461-6 (2001).

Lee et al., A nonneutralizing anti-HIV-1 antibody turns into a neutralizing antibody when expressed on the surface of HIV-1-susceptible cells: A new way to fight HIV, *J. Immunol.*, 173: 4618-26 (2004).

Liao et al., Design of trangenes for efficient expression of active chimeric proteins on mammalian cells, *Biotechnol. Bioengin.* 73(4): 313-23 (2001).

Lin et al., Receptor-specific targeting mediated by the coexpression of a targeted murine leukemia virus envelope protein and a binding-defective influenza hemagglutinin protein, *Hum. Gene Ther.*, 12(4): 323-32 (2001).

Liu et al., Immune control of an SIV challenge by a T-cell-based vaccine in rhesus monkeys. *Nat. Lett.*, 457: 87-91 (2009).

Lois et al., Germline transmission and tissue-specific expression of trangenes delivered by lentiviral vectors, *Science*, 295(5556): 868-72 (2002).

Lori et al., Cellular immunity and DNA vaccines for the treatment of HIV/AIDS, *Curr. Med. Chem. Anti-Infect. Agents*, 3: 31-41 (2004).

Lorimer et al., Targeting retrovirus to cancer cells expressing a mutant EGF receptor by insertion of a single chain antibody variable domain in the envelope glycoprotein receptor binding lobe, *J. Immunol. Meth.*, 237: 147-57 (2000).

Lu et al., Therapeutic dendritic-cell vaccine for chronic HIV-1 infection, Nature Medicine 10(12):1359-1365, 2004.

Lubong Sabado et al., Directing dendritic cell immunotherapy towards successful cancer treatment. *Immunotherapy*, 2(1): 37-56 (2010).

Lutzko et al., Lentivirus ventors incorporating the immunoglobulin heavy chain enhancer and matrix attachment regions provide position-independent expression in B lymphocytes, *j. Virol.*, 77: 7341-51 (2003).

Mangeot et al., Development of minimal lentivirus vectors derived from simian immunodeficiency virus (SIVmac251) an their use for gene transfer into human dendritic cells, *J. Virol.*, 74: 8307-15 (2000).

(56) References Cited

OTHER PUBLICATIONS

Marozsan et al., Relationships between infectious titer, capsid protein levels, and reverse transcriptase activities of diverse human immunodeficiency virus type 1 isolates. *J. Virol.*, 78(20): 11130-41 (2004).
Matano et al., Targeted infection of a retrovirus bearing a CD4-Env chimera into human cells expressing human immunodeficiency virus type 1, *J. Gen. Virol.*, 76: 3165-9 (1995).
Matsuno et al., A life stage of particle-laden rat dendritics in vivo: Their terminal division, active phagocytosis, and translocation from the liver to the draining lymph. *J. Exp. Med.*, 183: 1865-78 (1996).
Maurice et al., Efficient gene transfer into human primary blood lymphocytes by surface-engineered lentiviral vectors that display a T cell-activating polypeptide, *Blood*, 99(7): 2342-50 (2002).
McKnight et al., Deduced consensus sequence of Sindbis virus strain AR339: mutations contained in laboratory strains which affect cell culture and in vivo phenotypes, J. Virol. 70:1981-1989, 1996.
Meissner et al., Development of an inducible pol III transcription system essentially requiring a mutated form of the TATA-binding protein, *Nucl. Acids Res.*, 29(8): 1672-82 (2001).
Meyer zum Buschenfelde et al., Generation of tumor-reactive CTL against the tumor-associated antigen HER2 using retrovirally transduced dendritic cells derived from CD34+ hematopoietic profenitor cells, *J. Immunol.*, 165: 4311-40 (2000).
Miyoshi et al., Development of a self-inactivating lentivirus vector, J. Virol. 72:8150-8157, 1998.
Miyoshi et al., Transduction of human CD34+ cells that mediate long-term engraftment of NOD/SCID mice by HIV vectors, *Science*, 283(5402): 682-6 (1999).
Morizono et al., Antibody-Directed Targeting of Retroviral Vectors via Cell Surface Antigens, Viral. 75:8016-8020, 2001.
Morizono et al., Lentiviral vector retargeting to P-glycoprotein on metastatic melanoma through intravenous injection, Nature Medicine 11:346-352, 2005.
Morizono et al., Redirecting Lentiviral Vectors Pesudotyped with Sindbis virus-Derived Envelope Proteins to DC-SIGN by Modification of N-Linked Glycans of Envelope Proteins, Journal of Virology 84(14):6923-6934, 2010.
Mukhopadhyay et al., A structural perspective of the flavivirus life cycle, Nature Rev. 1 icrobial. 3:13-22, 2005.
Narayan et al., Biology and pathogenesis of lentiviruses. *J. Gen. Virol.*, 70: 1617-39 (1989).
Navaratnarajah et al., Functional characterization of the Sindbis virus E2 glycoprotein by transposon linker-insertion mutagenesis, Virology 363:134-147, 2007.
Negri et al. Successful immunization with a single injection of non-integrating lentiviral vector, Mol. Ther. 15:1716-1723, 2007.
Nussenzweig et al., Immune responses: Tails to teach a B cell, *Curr. Biol.*, 7: R355-7 (1997).
Nyberg-Hoffman et al., Sensitivity and reproducibility in adenoviral infectious titer determination. Nat. Med., 3(7): 808-11 (1997).
Ohno et al., Cell-specific targeting of Sindbis virus vectors displaying IgG-binding domains of protein A, Nature Biotechnology 15:763-767, 1997.
Palmer et al., Gene therapy for colorectal cancer. *Brit. Med. Bull.*, 64: 201-25 (2002).
Papagatsias et al., Activity of different vaccine-associated promoter elements in human dendritic cells, Immunol. Lett. 115:117-125, 2008.
Park et al., An essential role for Akt1 in dendritic cell function and tumor immunotherapy, *Nat. Biotechnol.*, 24(12): 1581-90 (2006).
Park et al., Five mouse homologues of the human dendritic cell C-type lectin, DC-SIGN, *Intl. Immunol.*, 13(10): 1283-90 (2001).
Paule et al., Transcription by RNA polymerase I and III, *Nucl. Acids Res.*, 28(6): 1283-98 (2000).
Pauwels, et al., State-of-the-Art Lentiviral Vectors for Research Use: Risk Assessment and Biosafety Recommendations, Current Gene Therapy 9:459-474, 2009.

Perri et al., An alphavirus replicon particle chimera derived from venezuelan equine encephalitis and sindbis viruses is a potent gene-based vaccine delivery vector, *J. Virol.*, 77(19): 10394-403 (2003).
Pfeifer et al., Gene therapy: promises and problems, Annu. Rev. Genomics Hum. Genet. 2:177-211, 2001.
Philippe et al., Lentiviral vectors with a defective integrase allow efficient and sustained transgene expression in vitro and in vivo, Proc. Natl. Acad. Sci. USA 103:17684-17689, 2006.
Pitisuttithum et al., HIV-1 prophylactic vaccine trials in Thailand. *Curr. HIV Res.*, 3(1): 17-30 (2005).
Powlesland et al., Widely divergent biochemical properties of the complete set of mouse DC-SIGN-related proteins, *J. Biol. Chem.*, 281: 20440-9 (2006).
Racaniello, Are all virus particles infectious? *Virology blog*, http://www.virology.ws/2011/01/21are-all-virus-particles-infectious/, Jan. 21, 2011.
Ready et al., AIDSVAX flop leaves vaccine field unscathed, *Nat. Med.*, 9(4): 376 (2003).
Reed et al., New horizons in adjuvants for vaccine development, Trends in Immunology 30:23-32, 2009.
Ribas et al., Cancer immunotherapy using gene-modified dendritic cells, *Curr. Gene Ther.*, 2: 57-78 (2000).
Rosenberg et al., Cancer immunotherapy moving beyong currect vaccines, *Nat. Med.*, 10: 909-15 (2004).
Rowe et al., Immunication with a lentiviral vector stimulates both CD4 and CD8 T cell responses to an ovalbumin trangene. *Molec. Ther.*, 13(2): 310-9 (2006).
Russell et al., Sindbis Virus mutations which coordinately affect glycoprotein processing, penetration and virulence in mice. *J. Virol.* 63(4): 1619-29 (1989).
Sanders, No false start for novel pseudotyped vectors. *Curr. Opin. Biotechol.*, 13(5): 437-42 (2002).
Sandrin et al., Targeting retroviral and lentiviral vectors. *Curr. Top. Microbiol. Immunol.*, 281: 137-78 (2003).
Sastry et al., Titering lentiviral vectors: Comparison of DNA, RNA and marker expression methods. Gene Ther., 9: 1155-62 (2002).
Schroers et al., Lentiviral transduction of human dendritic cells, *Meth. Mol. Biol.*, 246: 451-9 (2004).
Schuler et al., The use of dendritic cells in cancer immunotherapy, *Curr. Opin. Immunol.*, 15: 138-47 (2003).
Schwartz et al., Cloning and functional analysis of multiply spliced mRNA species of human immunodeficiency virus type 1, *J. Virol.*, 64(6): 2519-9 (1990).
Sharkey et al., Ross River Virus Glycoprotein-Pseudotyped Retroviruses and Stable Cell Lines for Their Production,I Virol. 75:2653-2659, 2001.
Shen et al., Silencing of SOCS1 enhances antigen presentation by dendritic cells and antigen-specific anti-tumor immunity. *Nat. Biotechnol.*, 22: 1546-53 (2004).
Shimizu et al., Internalization of kit together with stem cell factor on human fetal liver-derived mast cells: A new protein and RNA synthesis are required for reappearance of kit, *J. Immunol.*, 156: 3443-9 (1996).
Shiu et al., Identification of ongoing human immunodeficiency virus type 1 (HIV-1) replication in residual viremia during recombinant HIV-1 poxvirus immunications in patients with clinically undetectable viral loads on durable suppressive highly active antiretroviral therapy, *J. Virol.*, 83(19): 9731-42 (2009).
Shiver et al., Recent Advances in the Development of HIV-1 Vaccines Using Replication-Incompetent Adenovirus Vectors, Annu. Rev. Med. 55:355-372, 2004.
Shresta et al., Critical Roles for Both STAT1-Dependent and STAT I-Independent Pathways in the Control of Primary Dengue Virus Infection in Mice, The Journal of Immunology 175:3946-3954, 2005.
Skehel et al., Receptor binding and membrane fusion in virus entry: The influenza hemagglutinin et al., *Annu. Rev. Biochem.*, 69: 531-69 (2000).
Smit et al., PE2 Cleavage Mutants of Sindbis Virus: Correlation between Viral Infectivity and pH-Dependent Membrane Fusion Activation of the Spike Heterodimer,J. Virol. 75:11196-11204, 2001.
Smit et al., Low-pH-dependent fusion of Sindbis virus with receptor-free cholesterol- an sphingolipid-containing liposomes, *J. Virol.*, 73(10): 8476-84 (1999).

(56) References Cited

OTHER PUBLICATIONS

Somia et al., Generation of targeted retroviral vectors by using single-chain variable fragment—An approach to in vivo gene delivery, *Proc. Natl. Acad. Sci. USA*, 92: 7570-4 (1995).

Song et al., Persistent, antigen-specific, therapeutic antitumor immunity by dendritic cells genetically modified with an adenviral vector to express a model tumor antigen, *Gene Ter.*, 7: 2080-6 (2000).

Steinmann et al., Tolerogenic dendritic cells, *Annu. Rev. Immunol.*, 21: 685-711 (2003).

Strang et at, Human Immunodeficiency Virus Type 1 Vectors with Alphavirus Envelope Glycoproteins Produced from Stable Packaging Cells, I Virol. 79:1765-1771, 2005.

Strauss et al., The alphaviruses: gene expression, replication, and evolution, Microhiol. Rev. 58:491-562, 1994.

Strauss et al., Host-cell receptors for Sindbis virus. *Arch. Virol.*, 9: 473-84 (1994).

Stricker et al., The maginot line and AIDS vaccines, *Medical Hypotheses*, 48: 527-9 (1997).

Sutton et al., Human immunodeficiency virus type 1 vectors efficiently transduce human hematopoietic stem cells, *J. Virol.*, 72(7): 5781-8 (1998).

Tacken eta l., Dendritic-cell immunotherapy: From ex vivo loading to in vivo targeting, *Nat. Rev. Immunol.*, 7: 790-802 (2007).

Takadera et al., Structure of the two promoters of the human *Ick* gene: Differential accumulation of two classes of *Ick* transcripts in T cells, *Mol. Cell. Biol.*, 9(5): 2173-80 (1989).

Takahara et al., Functional comparison of the mouse DC-SIGN, SIGNR1, SIGNR3 and Langerin, C-type lectins, *Int. Immunol.*, 16: 819-29 (2004).

Tang et al., Molecular links between the E2 envelope glycoprotein and nucleocapsid core in Sindbis virus. *J. Molec. Biol.*, 414: 442-59 (2011).

Tatsis et al., Adenoviruses as vaccine vectors, *Mol. Ther.*, 10: 616-29 (2004).

Temme et al., Efficient transduction and long-term retroviral expression of the melanoma-associated tumor antigen tyrosinase in CD34(+) cord blood-derived dendritic cells, *Gene Ther.*, 9: 1551-50 (2002).

Trumpfheller et al., Intensified and protective CD4+ T cell immunity in mice with anti-dendritic cell HIV gag fusion antibody vaccine. *J. Exp. Med.*, 1-11 (2006).

Uchida et al., HIV, but not murine leukemia virus, vectors mediate high efficiency gene transfer into freshly isolated G0/G1 human hematopoietic stem cells, *Proc. Natl Acad. Sci. USA*, 95(20): 11939-44 (1998).

Valsesia-Wittmann et al., Modifications in the binding domain of avian retrovirus envelope protein to redirect the host range of retroviral vectors, *J. Virol.*, 68(7): 4609-19 (1994).

Veljkovic et al., AIDS epidemic at the beginning of the third millennium: Time for a new AIDS vaccine strategy, *Vaccine*, 19: 1855-62 (2001).

Verhoeyen et al., Surface-engineering of lentiviral vectors. *J. Gene Med.*, 6: S83-94 (2004).

Verma et al., Gene therapy—promises, problems and prospects, *Nature*, 389(6648): 239-42 (1997).

Waite et al., Inhibition of Sindbis virus release by media of low ionic strength: an electron microscope study. *J. Virol.*, 10(3): 537-44 (1972).

Wang et al., High-affinity laminin receptor is a receptor of Sindbis virus in mammalian cells, *J. Virol.*, 66: 4992-5001 (1992).

Weber et al., Phase I clinical trial with HIV-1 gp160 plasmid vaccine in HIV-1-infected asymptomatic subjects. *Eur. J. Clin. Microbiol. Infect. Dis.*, 20: 800-3 (2001).

West et al., Mutations in the endodomain of Sindbis virus glycoprotein E2 define sequences critical for virus assembly, J. Virol. 80:4458-4468, 2006.

Wigler et al., DNA-mediated transfer of the adenine phosphoribosyltransferase locus into mammalian cells, *Proc. Natl. Acad. Sci. USA*, 76(3): 1373-6 (1979).

Williamsburg BioProcessing Foundation, Reference Materials for Retroviruses and Lentiviruses—Final Report, pp. 1-13, Jun. 5, 2002.

Wu et al., Enhanced breadth of CD4 T-cell immunity by DNA prime adenovirus boost immunication to human immunodeficiency virus Env and Gag immunogens. *J. Virol.*, 79(13): 8024-31 (2005).

Yang et al., Engineered lentivector targeting of dendritic cells for in vivo immunization, Nature Biotechnology 26:326-334, 2008.

Yang et al., Targeted lentiviral vectors to specific cell types in vivo, Proc. Natl. Acad. Sci. USA 103(31):11479-11484, 2006.

Yang et al., Long-term in vivo provision of antigen-specific T cell immunity by programming hematopoietic stem cells, *Proc. Natl. Acad. Sci. USA*, 102: 4518-23 (2005).

Yee et al., The regulation of myogenin gene expression during the embryonic development of the mouse, *Genes Dev.*, 7: 1277-89 (1993).

You et al., Targeting dendritic cells to enhance DNA vaccine potency, *Cancer Res.*, 61: 3704-11 (2001).

Zarei et al., Transduction of dendritic cells by antigen-encoding lentiviral vectors permits antigen processing and MHC class I-dependent presentation, J. Allergy Clin. Immunol. 109:988-994, 2002.

Zennou et al., HIV-1 Genome Nuclear Import is Mediated by a Central DNA Flap, Cell 101:173-185, 2000.

Zhai et al., Antigen-specific tumor vaccines, *J. Immunol.*, 156(2): 700-10 (1996).

Zhou et al., Current methods for loading dendritic cells with tumor antigen for the induction of antitumor immunity. *J. Immunol.* 25(4): 289-303 (2002).

Zhou et al., DC-SIGN and immunoregulation. *Cell Mol. Immunoo.*, 3: 279-83 (2006).

Zimmerman et al., Identification of a host protein essential for assembly of immature HIV-1 capsids, *Lett. Nat.*, 415: 88-92 (2002).

Zufferey et al., Self-Inactivating Lentivirus Vector for Safe and Efficient In Vivo Gene Delivery, J. Viral. 72:9873-9880, 1998.

Zufferey et al., Woodchuck hepatitis cirus posttranscriptional regulatory element enhances expression of trangenes delievered by retroviral vectors, *J. Virol.*, 74(4): 2886-92 (1999).

\* cited by examiner

FIG. 3A

Influenza Virus Hemagglutinin Mutant (HAmu, Class I fusion)

| HA1 340 AAs | HA2 222 AAs | a1, a2, a3

FIG. 3C

Sindbis Virus Glycoprotein Mutant (SINmu, Class II fusion)

| E3 60 AAs | E2 71 AAs | HA Tag 10 AAs | E2 350 AAs | 6K 55 AAs | E1 439 AAs | a4, a5, a6

FIG. 3B

Gate on GFP+ Cells

- no transfection, ctrl: <1%
- FUGW+VSVG, ctrl: 99.7%
- FUGW+αCD20+HAmu: 95%

αCD20 vs GFP; HAmu vs GFP: 32%

FIG. 3D

Gate on GFP+ Cells

- no transfection, ctrl: <1%
- FUGW+VSVG, ctrl: 99%
- FUGW+αCD20+SINmu: 99%

αCD20 vs GFP; SINmu vs GFP: 20.8%

SEQUENCE LISTING

```
<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: Synthetic linker

<400> SEQUENCE: 1

Gly Gly Gly Gly Ser Gly Gly Gly Ser Gly Gly Gly Gly Ser Gly Gly
1               5                   10                  15

Gly Ser
```

METHOD OF TARGETED GENE DELIVERY USING VIRAL VECTORS

CROSS-REFERENCE TO RELATED APPLICATIONS

The present application claims priority under 35 U.S.C. §120 as a continuation of U.S. patent application Ser. No. 11/446,353, filed Jun. 1, 2006, now abandoned, which claims priority under 35 U.S.C. §119(e) to U.S. Provisional Application No. 60/686,215, filed Jun. 1, 2005 and U.S. Provisional Application No. 60/738,078, filed Nov. 19, 2005. All of the aforementioned priority applications are herein expressly incorporated by reference in their entirety.

BACKGROUND OF THE INVENTION

1. Field of the Invention

The invention relates generally to targeted gene delivery, and more particularly to the use of a recombinant virus comprising a fusogenic molecule and a distinct affinity molecule.

2. Description of the Related Art

The delivery of functional genes and other polynucleotides into particular target cells can be used in a variety of contexts. For example, gene therapy can be used to prevent or treat disease. A particularly desirable gene delivery protocol would be able to precisely deliver a gene of interest to specific cells or organs in vivo. Certain viruses are naturally suited for gene delivery, and significant effort has been focused on engineering viral vectors as gene transfer vehicles. Among these viruses, oncoretroviral and lentiviral vectors exhibit promising features because they have the ability to produce stable transduction, maintain long-term transgene expression and, for lentiviruses, enable transduction of non-dividing cells. Targeting such viruses to particular cell types has proved to be challenging.

Many attempts have been made to develop targetable transduction systems using retroviral and lentiviral vectors (see, for example, D. Lavillette, S. J. Russell, F. L. Cosset, Curr. Opin. Biotech. 12, 461 (2001), V. Sandrin, S. J. Russell, F. L. Cosset, Curr. Top. Microbio. Immunol. 281, 137 (2003)). Significant effort has been devoted to altering the envelope glycoprotein (env), the protein that is responsible for binding the virus to cell surface receptors and for mediating entry. The plasticity of the surface domain of env allows insertion of ligands, peptides and single-chain antibodies, which can direct the vectors to specific cell types (N. V. Somia, M. Zoppe, I. M. Verma, Proc. Natl. Acad. Sci. USA 92, 7570 (1995)). However, this manipulation adversely affects the fusion domain of env, resulting in low viral titers. The unknown and delicate coupling mechanisms of binding and fusion make it extremely difficult to reconstitute fusion function once the surface domain of the same molecule has been altered.

Another approach involves complex env with a ligand protein or antibody to form a bridge to attach the virus to specific cells (e.g., K. Morizono, G. Bristol, Y. M. Xie, S. K. P. Kung, I. S. Y. Chen, J. Virol. 75, 8016 (2001). The challenge to this approach is that env, once complexed with the one end of the bridge molecule, fuses inefficiently. Since no practical strategies are available for targeted in vivo gene delivery, current gene therapy clinical trails are generally based on in vitro transduction of purified cells followed by infusion of the modified cells into the patient. This in vitro approach is an expensive procedure with significant safety challenges.

SUMMARY OF THE INVENTION

According to one aspect of the invention, methods are provided for delivering a polynucleotide to a desired cell, comprising infecting a target cell with a recombinant retrovirus. In other aspects, recombinant retrovirus and various vectors and constructs for producing the recombinant retrovirus are provided.

The envelope of the recombinant retrovirus preferably comprises a fusogenic molecule and a cell-specific binding determinant. In some embodiments, the recombinant retrovirus preferably comprises the R and U5 sequences from a 5' lentiviral long terminal repeat (LTR), a self-inactivating lentiviral 3' LTR, a fusogenic molecule, and a cell-specific binding determinant. In some embodiments, the recombinant retrovirus is produced from the FUGW construct.

The fusogenic molecule is preferably a viral glycoprotein and may be, for example, a class I or class II fusogen. In some embodiments of the invention, the fusogenic molecule is pH sensitive. Preferably the pH sensitivity is such that the fusogen is able to mediate delivery of the viral core across the membrane in the endocytic compartment of a target cell. In some embodiments, the fusogenic molecule may have a lowered affinity for a cognate molecule, such as a receptor or antigen.

In some embodiments, the fusogenic molecule is hemagglutinin, preferably a mutant hemagglutinin. In other embodiments, the fusogenic molecule is SIN. In still other embodiments, the fusogenic molecule comprises a viral glycoprotein derived from one of the following viruses: Lassa fever virus, tick-borne encephalitis virus, Dengue virus, Hepatitis B virus, Rabies virus, Semliki Forest virus, Ross River virus, Aura virus, Borna disease virus, Hantaan virus, and SARS-CoV virus.

In some embodiments of the invention, the cell-specific binding determinant comprises a protein that is able to bind with specificity to a cell surface molecule present on a target cell. Preferably, the binding is high-affinity binding and in some embodiments the dissociation constant may be in the range of $10^{-6}$ to $10^{-12}$ M. However, in other embodiments lower or higher affinity binding is possible.

The cell-specific binding determinant is preferably a protein, and in some embodiments is an antibody. The cell-specific binding determinant may comprise more than one molecule. For example, if the cell-specific binding determinant comprises an antibody, it may also comprise immunoglobulin alpha and immunoglobulin beta. If the antibody is, for example, a single chain antibody, it may be fused with a transmembrane domain from another protein. In some particular embodiments of the invention, the antibody is a CD20 antibody, a CD34 antibody or an antibody against DEC-205.

In some embodiments of the invention, the 5' LTR sequences are from HIV. The self-inactivating 3' LTR may comprise a U3 element with a deletion of its enhancer sequence. The self-inactivating 3' LTR may be a modified HIV 3' LTR. The recombinant retrovirus may comprise other elements, such as the woodchuck hepatitis virus enhancer element sequence and/or a tRNA amber suppressor sequence.

The recombinant retrovirus may be pseudotyped, for example, with the vesicular stomatitits virus envelope glycoprotein or ecotropic envelope protein 4.17.

In preferred embodiments, the recombinant retrovirus further comprises one or more genes of interest to be delivered to the target cell. The gene of interest is not limited in any way, and may, for example, encode a protein to be expressed in the cell. In other embodiments the gene of interest encodes an siRNA or other molecule to be expressed in the cell. In some embodiments at least one of the genes of interest is a reporter gene, such as a fluorescent protein. In some embodiments, the fluorescent protein is green fluorescent protein.

The gene of interest is preferably linked to a promoter, such as an RNA Polymerase II or a Polymerase III promoter. In some embodiments, the promoter is a ubiquitous promoter. For example, the ubiquitous promoter may be selected from the group consisting of the ubiquitin promoter, the CMV β-actin promoter and the pgk promoter. In other embodiments the promoter may be a tissue specific promoter. A tissue specific promoter, if present, may, for example, be selected from the group consisting of the lck promoter, the myogenin promoter and the thy1 promoter.

The recombinant retrovirus may additionally comprise an enhancer operably linked to the promoter. In some embodiments, the enhancer and promoter are both CMV sequences.

In some embodiments of the invention, a packaging cell line is transfected with one or more vectors encoding the retroviral elements, the gene of interest, the fusogenic molecule and the cell-specific binding determinant. Recombinant retrovirus is collected from the packaging cell line and used to infect target cells, thereby delivering the gene of interest to the target cells. In some embodiments of the invention, the packaging cell line is a 293 cell line.

BRIEF DESCRIPTION OF THE DRAWINGS

FIG. 3A illustrates the fusion protein HAmu derived from influenza A (FPV) hemagglutinin (HA). HA contains two glycoproteins after maturation: HA1 for binding to cell surface receptor, sialic acid; and HA2 for triggering membrane fusion. Three point mutations within the receptor binding sites (a1: Y106F, a2: E199Q, a3: G237K) were introduced to generate a binding-defective but fusion-competent fusogenic molecule (HAmu).

FIG. 3B illustrates a FACS analysis of virus-producing cells. 293T cells that were transiently transfected with separate plasmids encoding the following: the lentiviral vector FUGW; the membrane-bound antibody αCD20; the accessory proteins Igα and Igβ; the fusion protein HAmu; and viral gag, pol, and rev genes. Expression of αCD20 and HAmu was detected using anti-human IgG antibody and anti-FPV HA antibody.

FIG. 3C illustrates the fusion protein SINmu derived from Sindbis viral glycoprotein (SIN). SIN contains two membrane glycoproteins (E1 and E2) and a signal peptide (E3): E1 for mediating fusion; E2 for receptor binding; E3 as a signal sequence for processing of E2 glycoprotein. A ten-residue detection tag sequence was inserted between amino acid 71 and 74 of the E2 glycoprotein. A series of alterations (a4: deletion of amino acids 61-64 of E3; a5: mutation of 68SLKQ71 into 68AAAA71; ab: mutation of 157KE158 into 157AA158) was introduced to yield the binding defective and fusion competent SINmu fusion molecule.

FIG. 3D is similar to the FACS analysis shown in FIG. 3B, except that SINmu was used for the fusion protein and was detected by an anti-tag antibody.

FIG. 6A illustrates expression of a gene of interest (GFP) in fresh, unfractionated human PBMCs ($2 \times 10^6$) transduced by co-culturing with concentrated FUGW/αCD20+SINmu, CCMV/αCD20+SINmu or CPGK/αCD20+SINmu virus ($10 \times 10^6$ TU). LPS (50 μg/mL) was added into the culture media for B cell survival and growth. After two days, the B cell population was identified by co-staining of CD19 and CD20. The solid line indicates expression in transduced cells; the shaded line shows expression in untransduced cells.

FIG. 6B shows stable integration of the transgene as detected by genomic PCR amplification using a pair of GFP-specific primers.

FIG. 6C shows expression of a gene of interest in target cells following in vivo delivery of virus. Fresh human PBMCs were transferred into irradiated RAG2$^{-/-}\gamma_c^{-/-}$ mice ($100 \times 10^6$/mouse) via tail vein injection. Six hours later, concentrated virus ($100 \times 10^6$ TU/mouse) was injected through the tail vein. Two days later, whole blood was collected from these mice via heart puncture and the cells were stained for human CD3 and CD20 and then analyzed by FACS for GFP expression. In the lower panels, the shaded line illustrates no virus treatment and the dashed line shows treatment with FUGW/b12+ SINmu virus. The solid line shows treatment with FUGW/αCD20+SINmu virus.

DETAILED DESCRIPTION

Targeting efficient gene delivery vehicles to the desired cell types with specificity greatly enhances the therapeutic potential of virus-mediated gene therapy and alleviates concerns of off-target effects in vivo. In addition, it has many advantages in other contexts, such as in the generation of transgenic animals with particular traits, such as disease resistance or production of a protein in specific tissues.

The preferred embodiments of the methods and constructs described herein are based, in part, on the finding that the viral binding and fusion functions can be separated into two distinct components (fusogenic proteins and affinity molecules) that are inserted into the viral envelope. This allows precise targeting of virus to the desired target cells and efficient transduction and delivery of a desired polynucleotide or other molecule. An advantage of this method over others, for example those where viral fusion proteins are engineered with a foreign binding component, is that the fusion protein can maintain its biological activity so that viral titer is not sacrificed for increased target specificity.

Figure 1:
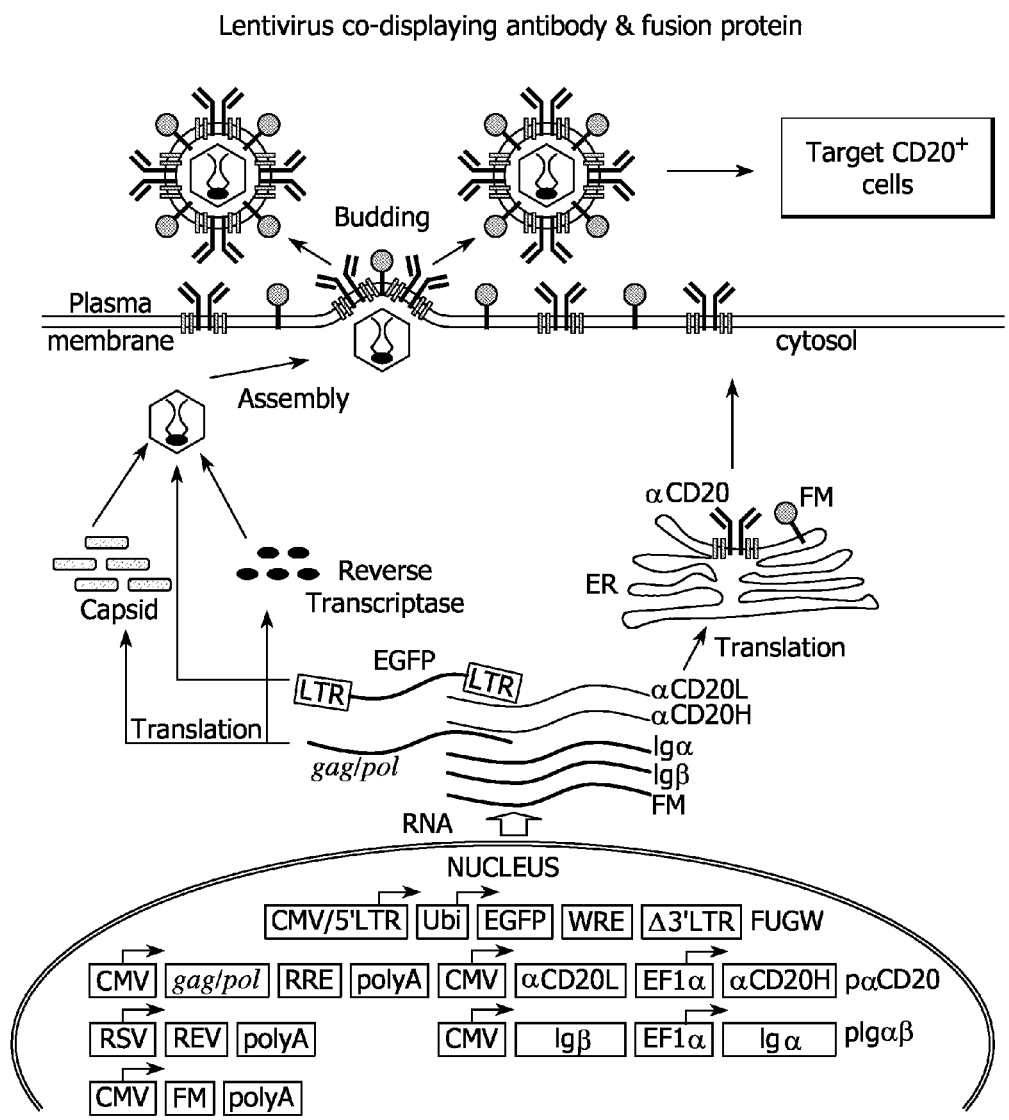
FIG. 1 is a schematic representation of the generation of recombinant virus bearing a cell-specific binding determinant and a fusogenic molecule according to some embodiments of the invention.
Figure 2:
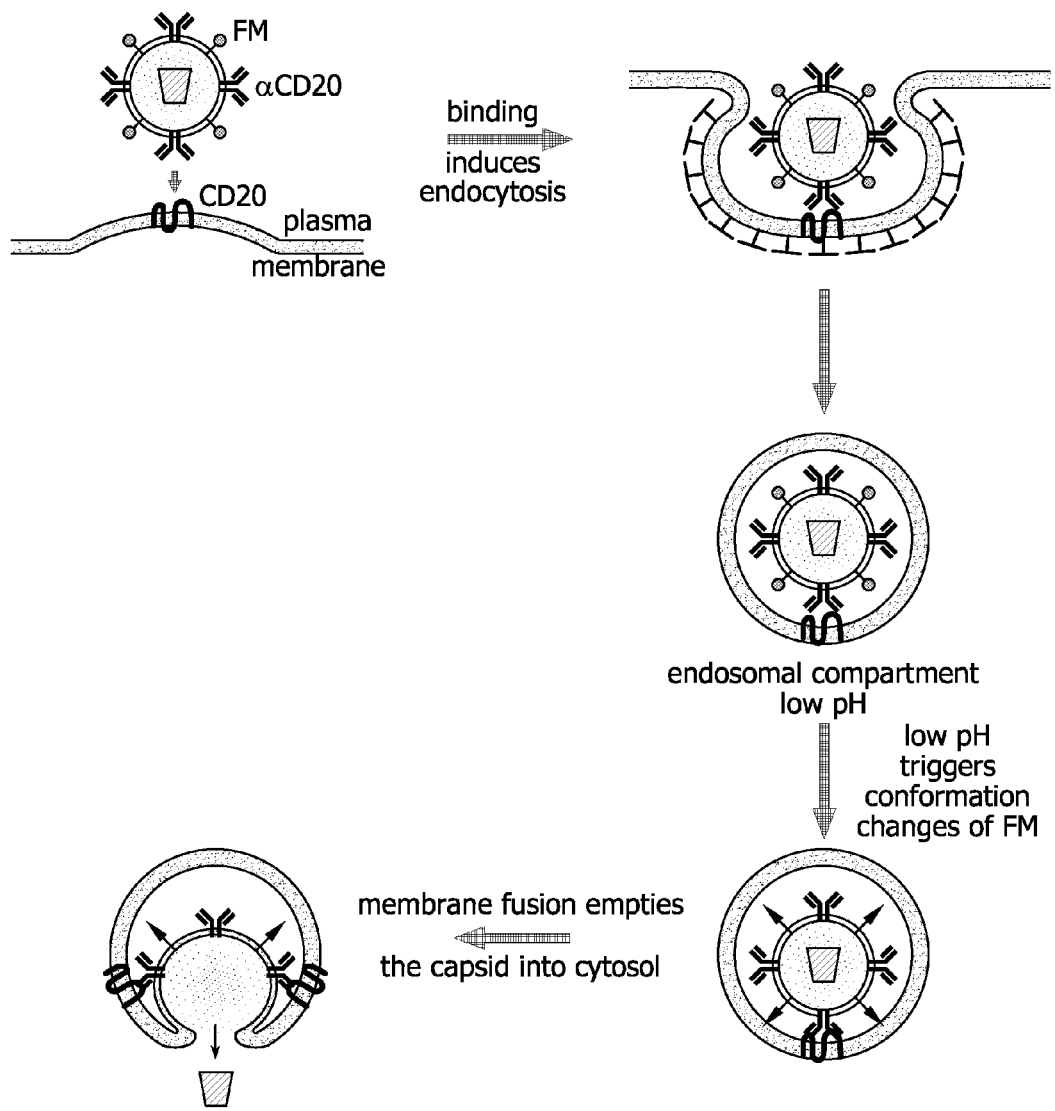
FIG. 2 illustrates a molecular mechanism of targeted transduction of a viral particle that includes a fusogenic molecule and an affinity molecule.

As discussed in detail below, the methods are preferably based on the use of recombinant retroviruses, such as lentiviruses, because these viruses readily incorporate into their envelope whatever proteins are found on the surface of virus-producing cells. However, other types of viruses may be used and the methods modified accordingly. Generally, a packaging cell line is transfected with one or more vectors encoding the retroviral components, a gene of interest, a fusion molecule and an affinity molecule. During budding of the virus the fusion molecule and affinity molecule, which have been expressed in the packaging cell membrane, are incorporated into the viral envelope (FIG. 1). As a result, the retroviral particles comprise a core including the gene of interest and an envelope comprising the fusion molecule and the affinity molecule on its surface. The affinity molecule then recognizes a constituent of the target cell membrane and attaches the lentivirus to the cell surface (FIG. 2). The binding induces endocytosis of the target, bringing the lentivirus into an endosome. There, the fusogenic molecule (FM) triggers membrane fusion, allowing the virus core to enter the cytosol. Following reverse transcription and migration of the product to the nucleus, the genome of the virus integrates into the target cell genome, incorporating the transgene.

The methods disclosed herein may be readily adopted to a variety of affinity molecules and fusogenic molecules. In a preferred embodiment, the fusion molecule (FM) is preferably a viral glycoprotein that mediates fusion, preferably in response to the low pH environment of the endosome, and the affinity molecule is preferably a membrane-bound protein that is efficiently endocytosed after binding. The fusion molecule preferably exhibits fast enough kinetics that the viral contents can empty into the cytosol before the degradation of the viral particle. In addition, the fusion molecule can be modified to reduce their binding ability and thus reduce or eliminate any non-specific binding. That is, by reducing the binding ability of the fusion molecules, binding of the virus to the target cell is determined predominantly or entirely by the affinity molecule, allowing for high target specificity and reducing undesired effects.

Affinity molecules may include, for example, antibodies to a particular antigen on the target cell surface, as well as receptors for cell surface ligands or ligands for cell surface receptors. The affinity molecules are preferably membrane bound. Thus, if an antibody is to be used it may be modified to membrane bound form. For example, the variable regions from an antibody with the desired specificity can be cloned into IgG$_1$. Alternatively, a transmembrane domain may be attached to an antibody, such as a single chain antibody.

In some embodiments, the methods are used to target dendritic cells using a membrane-bound monoclonal antibody against the DEC-205 receptor as the affinity molecule. In other embodiments, incorporation of a membrane-bound form of stem cell factor as the affinity molecule may be used to target c-kit-positive cells.

The modular flexibility (combination of affinity molecule and fusogenic molecule) and breadth (availability of, for example, monoclonal antibodies or ligands for many endocytosed cell-specific surface molecules, and the ability to generate such antibodies) of the disclosed method is thus especially advantageous in facilitating the application of targeted gene delivery for therapy, industry and research. For example, the methods of the present invention may be used to target tumor cells and deliver a toxic gene. In another embodiment, cells infected by a pathogen (or susceptible to such infection) may be targeted to deliver siRNA to inhibit a stage in the pathogen's life cycle. In still another embodiment, a cell lacking a particular component (e.g., an enzyme) may be targeted to deliver a gene encoding for that particular component.

Definitions

Unless defined otherwise, technical and scientific terms used herein have the same meaning as commonly understood by one of ordinary skill in the art to which this invention belongs. See, e.g., Singleton et al., *Dictionary of Microbiology and Molecular Biology 2nd ed.*, J. Wiley & Sons (New York, N.Y. 1994); Sambrook et al., *Molecular Cloning, A Laboratory Manual*, Cold Springs Harbor Press (Cold Springs Harbor, N.Y. 1989). Any methods, devices and materials similar or equivalent to those described herein can be used in the practice of this invention.

As used herein, the terms nucleic acid, polynucleotide and nucleotide are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages.

The terms nucleic acid, polynucleotide and nucleotide also specifically include nucleic acids composed of bases other than the five biologically occurring bases (adenine, guanine, thymine, cytosine and uracil).

As used herein, a nucleic acid molecule is said to be "isolated" when the nucleic acid molecule is substantially separated from contaminant nucleic acid molecules encoding other polypeptides.

"Immunization" refers to the provision of antigen to a host. In some embodiments, antigen is provided to antigen-presenting cells, such as dendritic cells. For example, as described below, recombinant virus comprising a gene encoding an antigen can be targeted to dendritic cells with an affinity molecule specific to a protein on dendritic cells. Thus the antigen to which an immune response is desired can be delivered to the dendritic cells. Other methods of immunization are well known in the art.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies" and "native immunoglobulins" are usually heterotetrameric glycoproteins, composed of two identical light (L) chains and two identical heavy (H) chains. Each light chain is linked to a heavy chain by a disulfide bond. The number of disulfide linkages varies among the heavy chains of different immunoglobulin isotypes. Each heavy chain comprises a variable domain ($V_H$) followed by a number of constant domains. Each light chain comprises a variable domain at one end ($V_L$) and a constant domain at its other end. The constant domain of the light chain is aligned with the first constant domain of the heavy chain, and the light chain variable domain is aligned with the variable domain of the heavy chain.

The term "antibody" is used in the broadest sense and specifically covers human, non-human (e.g. murine) and humanized monoclonal antibodies (including full length monoclonal antibodies), polyclonal antibodies, multi-specific antibodies (e.g., bispecific antibodies), single-chain antibodies, and antibody fragments so long as they exhibit the desired biological activity.

"Target cells" are any cells in which expression of a gene of interest is desired. Preferably, target cells exhibit a protein or other molecule on their surface that allows the cell to be targeted with an affinity molecule, as described below.

The term "mammal" is defined as an individual belonging to the class Mammalia and includes, without limitation, humans, domestic and farm animals, and zoo, sports, and pet animals, such as sheep, dogs, horses, cats and cows.

A "subject" or "patient" is any animal, preferably a mammal, that is in need of treatment.

As used herein, "treatment" is a clinical intervention made in response to a disease, disorder or physiological condition manifested by a patient or to be prevented in a patient. The aim of treatment includes the alleviation and/or prevention of symptoms, as well as slowing, stopping or reversing the progression of a disease, disorder, or condition. "Treatment" refers to both therapeutic treatment and prophylactic or preventative measures. Those in need of treatment include those already affected by a disease or disorder or undesired physiological condition as well as those in which the disease or disorder or undesired physiological condition is to be prevented. "Treatment" need not completely eliminate a disease, nor need it completely prevent a subject from catching the disease or disorder.

"Tumor," as used herein, refers to all neoplastic cell growth and proliferation, whether malignant or benign, and all precancerous and cancerous cells and tissues.

The term "cancer" refers to a disease or disorder that is characterized by unregulated cell growth. Examples of cancer include, but are not limited to, carcinoma, lymphoma, blastoma and sarcoma. Examples of specific cancers include, but are not limited to, lung cancer, colon cancer, breast cancer, testicular cancer, stomach cancer, pancreatic cancer, ovarian cancer, liver cancer, bladder cancer, colorectal cancer, and prostate cancer. Additional cancers are well known to those of skill in the art.

A "vector" is a nucleic acid that is capable of transporting another nucleic acid. Vectors may be, for example, plasmids, cosmids or phage. An "expression vector" is a vector that is capable of directing expression of a protein encoded by one or more genes carried by the vector when it is present in the appropriate environment.

The term "regulatory element" and "expression control element" are used interchangeably and refer to nucleic acid molecules that can influence the transcription and/or translation of an operably linked coding sequence in a particular environment. These terms are used broadly and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells may include, without limitation, promoters, enhancers, splicing signals and polyadenylation signals.

The term "transfection" refers to the introduction of a nucleic acid into a host cell.

"Retroviruses" are viruses having an RNA genome.

"Lentivirus" refers to a genus of retroviruses that are capable of infecting dividing and non-dividing cells. Several examples of lentiviruses include HIV (human immunodeficiency virus: including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates.

A "hybrid virus" as used herein refers to a virus having components from one or more other viral vectors, including element from non-retroviral vectors, for example, adenoviral-retroviral hybrids. As used herein hybrid vectors having a retroviral component are to be considered within the scope of the retroviruses.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, "RNA Viruses: A Practical Approach" (Alan J. Cann, Ed., Oxford University Press, (2000)), O Narayan and Clements J. Gen. Virology 70:1617-1639 (1989), Fields et al. Fundamental Virology Raven Press. (1990), Miyoshi H, Blomer U, Takahashi M, Gage F H, Verma I M. *J. Virol.* 72(10):8150-7 (1998), and U.S. Pat. No. 6,013,516.

Lentiviral vectors are known in the art, including several that have been used to transfect hematopoietic stem cells. Such vectors can be found, for example, in the following publications, which are incorporated herein by reference: Evans J T et al. *Hum Gene Ther* 1999; 10:1479-1489; Case S S, Price M A, Jordan C T et al. *Proc Natl Acad Sci USA* 1999; 96:2988-2993; Uchida N, Sutton R E, Friera A M et al. Proc Natl Acad Sci USA 1998; 95:11939-11944; Miyoshi H, Smith K A, Mosier D E et al. *Science* 1999; 283:682-686; Sutton R E, Wu H T, Rigg R et al. Human immunodeficiency virus type 1 vectors efficiently transduce human hematopoietic stem cells. *J Virol* 1998; 72:5781-5788.

"Virion," "viral particle" and "retroviral particle" are used herein to refer to a single virus comprising an RNA genome, pol gene derived proteins, gag gene derived proteins and a lipid bilayer displaying an envelope (glyco)protein. The RNA genome is usually a recombinant RNA genome and thus may contain an RNA sequence that is exogenous to the native viral genome. The RNA genome may also comprise a defective endogenous viral sequence.

A "pseudotyped" retrovirus is a retroviral particle having an envelope protein that is from a virus other than the virus from which the RNA genome is derived. The envelope protein may be from a different retrovirus or from a non-retroviral virus. A preferred envelope protein is the vesicular stomatitius virus G (VSV G) protein. However, to eliminate the possibility of human infection, viruses can alternatively be pseudotyped with an ecotropic envelope protein that limits infection to a specific species, such as mice or birds. For example, in one embodiment, a mutant ecotropic envelope protein is used, such as the ecotropic envelope protein 4.17 (Powell et al. Nature Biotechnology 18(12):1279-1282 (2000)).

A "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. Self-inactivating 3' LTRs are described, for example, in Zufferey et al. *J. Virol.* 72:9873-9880 (1998), Miyoshi et al. *J. Virol.* 72:8150-8157 and Iwakuma et al. *Virology* 261:120-132 (1999).

"Transformation," as defined herein, describes a process by which exogenous DNA enters a target cell. Transformation may rely on any known method for the insertion of foreign nucleic acid sequences into a prokaryotic or eukaryotic host cell and may include, but is not limited to, viral infection, electroporation, heat shock, lipofection, and particle bombardment. "Transformed" cells include stably transformed cells in which the inserted DNA is capable of replication either as an autonomously replicating plasmid or as part of the host chromosome. Also included are cells that transiently express a gene of interest.

A "fusogenic molecule," as described herein, is any molecule on a viral surface that triggers membrane fusion, and allows the virus core to pass through the membrane and, typically, enter the cytosol of a target cell. Viral glycoproteins are one example of fusogenic molecules.

An "affinity molecule," or "cell-specific binding determinant" as described herein, is any molecule on a viral surface that functions to recognize a molecular constituent on a target cell membrane and thereby target the virus to the cell surface. The affinity molecule is most preferably discrete from the fusogenic molecule.

By "transgene" is meant any nucleotide sequence, particularly a DNA sequence, that is integrated into one or more chromosomes of a host cell by human intervention, such as by the methods of the present invention. The transgene preferably comprises a "gene of interest." In other embodiments the transgene can be a nucleotide sequence, preferably a DNA sequence, that is used to mark the chromosome where it has integrated. The transgene does not have to comprise a gene that encodes a protein that can be expressed.

A "gene of interest" is not limited in any way and may be any nucleic acid, without limitation, that is desired to be integrated, transcribed, translated, and/or expressed in a target cell. The gene of interest may encode a functional product, such as a protein or an RNA molecule. Preferably the gene of interest encodes a protein or other molecule the expression of which is desired in the host cell. The gene of interest is generally operatively linked to other sequences that are useful for obtaining the desired expression of the gene of interest, such as transcriptional regulatory sequences.

A "functional relationship" and "operably linked" mean, without limitation, that the gene is in the correct location and orientation with respect to the promoter and/or enhancer that expression of the gene will be affected when the promoter and/or enhancer is contacted with the appropriate molecules.

An "RNA coding region" is a nucleic acid that can serve as a template for the synthesis of an RNA molecule, such as an siRNA. Preferably, the RNA coding region is a DNA sequence.

A "small interfering RNA" or "siRNA" is a double-stranded RNA molecule that is capable of inhibiting the expression of a gene with which it shares homology. In one embodiment the siRNA may be a "hairpin" or stem-loop RNA molecule, comprising a sense region, a loop region and an antisense region complementary to the sense region. In other embodiments the siRNA comprises two distinct RNA molecules that are non-covalently associated to form a duplex.

"2A sequences" or elements are small peptides introduced as a linker between two proteins, allowing autonomous intraribosomal self-processing of polyproteins (de Felipe. Genetic Vaccines and Ther. 2:13 (2004); deFelipe et al. Traffic 5:616-626 (2004)). The short peptides allow co-expression of multiple proteins from a single vector, such as co-expression of a fusogenic molecule and affinity molecule from the same vector. Thus, in some embodiments polynucleotides encoding the 2A elements are incorporated into a vector between polynucleotides encoding proteins to be expressed.

Fusogenic Molecules

Fusogenic molecules (FMs) are molecules that are able to be incorporated in the envelope of recombinant viruses and, under the right conditions, induce membrane fusion allowing entry of a gene of interest to a target cell. Fusogenic molecules preferably are able to pseudotype virus, preferably recombinant lentivirus and thus are able to be incorporated in the viral envelope. Preferably, the FM does not mediate viral infection of target cells directly, but still maintains its capability to induce fusion once a virus enters the endocytic pathways. Thus, while FMs may natively have the ability to bind a cell surface molecule, FMs with low or reduced binding ability are preferred to reduce non-specific transduction. Preferred FMs are viral glycoproteins. In addition, FMs are preferably resistant to ultracentrifugation to allow concentration, which is important for in vivo gene delivery.

FMs preferably induce membrane fusion at a low pH, independently of affinity molecule binding. Thus, in the disclosed methods FM induced membrane fusion preferably occurs once the virus comprising the FM is inside the endosome of a target cell and the viral core component, including a gene of interest, is delivered to the cytosol.

In some embodiments a tag sequence is incorporated into the fusogenic molecule to allow detection of FM expression and the presence of the FM in viral particles.

There are two recognized classes of viral fusogens and both can be used as FMs (D. S. Dimitrov, Nature Rev. Microbio. 2, 109 (2004)). The class I fusogens trigger membrane fusion using helical coiled-coil structures whereas the class II fusogens trigger fusion with β barrels. These two structures have different mechanics and kinetics (D. S. Dimitrov, Nature Rev. Microbio. 2, 109 (2004)).

Some non-limiting examples of surface glycoproteins that may be used as fusion molecules include glycoproteins from alphaviruses, such as Semliki Forest virus (SFV), Ross River virus (RRV) and Aura virus (AV), which comprise surface glycoproteins such as E1, E2, and E3. The E2 glycoproteins derived from the Sindbis virus (SIN) and the hemagglutinin (HA) of influenza virus are non-retroviral glycoproteins that recognize particular molecules on cell surfaces (heparin sulfate glycosaminoglycan for E2, sialic acid for HA) and are used as FMs in some embodiments. Their fusion is relatively independent of binding to receptor molecules, and the activation of fusion is accomplished through acidification in the endosome (Skehel and Wiley, Annu. Rev. Biochem. 69, 531-569 (2000); Smit, J. et al. J. Virol. 73, 8476-8484 (1999)). Moreover, they can tolerate certain genetic modifications and remain efficiently assembled on the retroviral surface (Morizono et al. J. Virol. 75, 8016-8020). Because of the ubiquitous presence of surface molecules recognized by some FMs, binding-defective but fusion competent fusogenic proteins are preferably used, such as a binding-defective form of HA.

In other embodiments of the invention, surface glycoproteins of Lassa fever virus, Hepatitis B virus, Rabies virus, Borna disease virus, Hantaan virus, or SARS-CoV virus may also be utilized as fusion molecules. In other embodiments, DV glycoprotein may be utilized as a fusion molecule.

In other embodiments of the invention, flavivirus-based surface glycoproteins may be used as fusion molecules. Like alphaviruses, flaviviruses use the class II fusion molecule to mediate infection (Mukhopadhyay et al. (2005) Rev. Microbio. 3, 13-22). prM (about 165 amino acids) and E (about 495 amino acids) are the glycoproteins of flaviviruses. Also, the ligand-binding pocket for DV has been well-characterized. Of interest, DC-SIGN (dendritic-cell-specific ICAM-grabbing non-integrin), a mannose-specific lectin, has been suggested to specifically interact with the carbohydrate residues on the DV E protein to enhance viral entry (Mukhopadhyay et al. (2005) Nat. Rev. Microbio. 3, 13-22). This, lentiviruses enveloped only by DV E protein can potentially target DCs. The ligand-binding pockets of TBE and DV E proteins, as well as other fusion molecules described, may be engineered to be binding deficient and fusion competent in the following manner.

In some embodiments, hemagglutinin (HA) from influenza A/fowl plague virus/Rostock/34 (FPV), a class I fusogen, is used. (T. Hatziioannou, S. Valsesia-Wittmann, S. J. Russell, F. L. Cosset, J. Virol. 72, 5313 (1998)). Preferably, a binding defective version of FPV HA, such as HAmu (FIG. 3A), is used (A. H. Lin et al., Hum. Gene. Ther. 12, 323 (2001)). HAmu-mediated fusion is generally considered to be independent of receptor binding (D. Lavillette, S. J. Russell, F. L. Cosset, Curr. Opin. Biotech. 12, 461 (2001)).

In other embodiments, a class II FM is used, preferably the Sindbis virus glycoprotein from the alphavirus family (K. S. Wang, R. J. Kuhn, E. G. Strauss, S. Ou, J. H. Strauss, J. Virol. 66, 4992 (1992)), herein also referred to as SIN. SIN includes two transmembrane proteins (S. Mukhopadhyay, R. J. Kuhn, M. G. Rossmann, Nature Rev. Microbio. 3, 13 (2005)), a first protein responsible for fusion (E1), and a second protein for cell binding (E2). SIN is known to pseudotype both oncoretroviruses and lentiviruses.

In some embodiments a binding-deficient and fusion-competent SIN is used as the fusogenic molecule. For example, a SIN fusogenic molecule can be used in which the immunoglobulin G binding domain of protein A (ZZ domain) is incorporated into the E2 protein and one or more additional mutations are made to inactivate the receptor binding sites (K. Morizono et al., Nature Med. 11, 346 (2005)).

The gene encoding the FM is preferably cloned into an expression vector, such as pcDNA3 (Invitrogen). Packaging cells, such as 293T cells are then co-transfected with the viral vector comprising the gene of interest, a packaging vector (if necessary), one or more vectors encoding an affinity molecule and any associated components, and the vector for expression of the fusogenic molecule. The FM is expressed on the membrane of the packaging cell and incorporated into the recombinant virus. Expression of envelope glycoprotein on the packaging cell surface may be analyzed by FACS.

Based on information obtained, for example from structural studies and molecular modeling, mutagenesis may be employed to generate the mutant forms of glycoproteins that maintain their fusogenic ability but have the desired level of binding. Several mutants may be created for each glycoprotein and assayed using the methods described below, or other methods known in the art, to identify FMs with the most desirable characteristics.

To select suitable FMs (either wild-type or mutant), viruses bearing both the FM and an affinity molecule are prepared and tested for their selectivity and/or their ability to facilitate penetration of the target cell membrane. Viruses that do not display the affinity molecule may be used as controls for measuring selectivity, while viruses displaying the affinity molecule and wild-type glycoprotein can be used as controls for examining titer effects in mutants. Cells expressing the binding partner of the affinity molecule are transduced by the virus using a standard infection assay. After a specified time, for example, 48 hours post-transduction, cells can be collected and the percentage of cells infected by the virus comprising the mutant FM can be determined by, for example, FACS. The selectivity can be scored by calculating the percentage of cells infected by virus. Similarly, the effect of mutations on viral titer can be quantified by dividing the percentage of cells infected by virus comprising a mutant FM by the percentage of cells infected by virus comprising the corresponding wild type FM. A preferred mutant will give the best combination of selectivity and infectious titer. Once an FM is selected, viral concentration assays may be performed to confirm that viruses enveloped by the FM can be concentrated. Viral supernatants are collected and concentrated by ultracentrifugation. The titers of viruses can be determined by limited dilution of viral stock solution and transduction of cells expressing the binding partner of the affinity molecule.

In some embodiments, BlaM-Vpr fusion protein may be utilized to evaluate viral penetration, and thus the efficacy of a fusion molecule (wild-type or mutant). An affinity molecule, such as an antibody, may envelope viral particles incorporating BlaM-Vpr. Such virus may be prepared, for example, by transient transfection of packaging cells with one or more vectors comprising the viral elements, BlaM-Vpr, the FM of interest and an affinity molecule. The resulting viruses can be used to infect cells expressing a molecule recognized by the affinity molecule in the absence or presence of the free inhibitor of affinity molecule binding (such as an antibody). Cells can then be washed with $CO_2$-independent medium and loaded with CCF2 dye (Aurora Bioscience). After incubation at room temperature to allow completion of the cleavage reaction, the cells can be fixed by paraformaldehyde and analyzed by FACS and microscopy. The presence of blue cells indicates the penetration of viruses into the cytoplasm; fewer blue cells would be expected when blocking antibody is added.

To investigate whether penetration is dependent upon a low pH, and select FM with the desired pH dependence, $NH_4Cl$ or other compound that alters pH can be added at the infection step ($NH_4Cl$ will neutralize the acidic compartments of endosomes). In the case of $NH_4Cl$, the disappearance of blue cells will indicate that penetration of viruses is low pH-dependent.

In addition, to confirm that the fusion molecule activity is pH-dependent, lysosomotropic agents, such as ammonium chloride, chloroquine, concanamycin, bafilomycin A1, monensin, nigericin, etc., may be added into the incubation buffer. These agents can elevate the pH within the endosomal compartments (e.g., Drose and Altendorf, J. Exp. Biol. 200, 1-8, 1997). The inhibitory effect of these agents will reveal the role of pH for viral fusion and entry. The different entry kinetics between viruses displaying different fusogenic molecules may be compared and the most suitable selected for a particular application.

PCR entry assays may be utilized to monitor reverse transcription and thus measure kinetics of viral DNA synthesis as an indication of the kinetics of viral entry. For example, viral particles comprising a particular FM and an affinity molecule may be incubated with packaging cells, such as 293T cells, expressing the appropriate cognate for the affinity molecule. Either immediately, or after incubation (to allow infection to occur) unbound viruses are removed and aliquots of the cells are analyzed. DNA may then be extracted from these aliquots and semi-quantitative performed using LTR-specific primers. The appearance of LTR-specific DNA products will indicate the success of viral entry and uncoating.

Cell-Specific Binding Determinants (Membrane-Bound Affinity Molecules)

In preferred embodiments of the invention, the viral surface comprises a cell-specific binding determinant comprising a membrane-bound affinity molecule. The affinity molecule is selected to bind selectively to a surface molecule, for example, a receptor protein, on a target cell. Preferably, the binding is high-affinity binding and in some embodiments the dissociation constant may be in the range of $10^{-6}$ to $10^{-12}$ M. However, in other embodiments lower or higher affinity binding is possible.

Generally, the target cell protein is one that is expressed selectively on the target cells. That is, the target cell protein is preferably expressed exclusively on target cells or expressed on target cells at a higher concentration than on other cells. However, in some embodiments where a wide population of target cells is to be targeted, a target cell protein may be expressed in a variety of cell types, or even ubiquitously expressed.

The affinity molecule is preferably a membrane-bound ligand, membrane bound receptor, or a membrane bound antibody, such as, without limitation, a chimeric antibody, an antibody fragment or a single chain antibody. Although referred to generally in the singular, the affinity molecule may comprise two or more molecules, such as an $IgG_1$ and the Igα and Igβ molecules.

The membrane-bound affinity molecule is most preferably a separate molecule from the fusogenic molecule.

Upon binding of the affinity molecule to a molecule on the target cell surface, the virus particle is taken up by endocytosis. In some embodiments, a pH change then induces the fusion molecule to fuse and allows the delivery of the viral core across the membrane and into the cytosol.

The affinity molecule is co-expressed in the packaging cell with the virus comprising the gene of interest and a fusogenic molecule. Constructs for expressing the affinity molecule in the packaging cell also may include, in some embodiments, sequences encoding necessary signal peptides to direct the protein to be expressed on the cell surface.

Packaging cells, such as 293T cells, are preferably co-transfected with the viral vector comprising the gene of interest, a packaging vector (if necessary), one or more vectors encoding the affinity molecule and any associated components (such as Igα and Igβ, and the vector for expression of the fusogenic molecule. In some embodiments, two or more of these components are combined in a multi-cistronic expression vector. For example, in some embodiments the fusogenic molecules and the affinity molecule are included in the same vector.

The affinity molecule is expressed on the membrane of the packaging cell and incorporated into the envelope of the recombinant virus. Expression of the affinity molecule may be assayed by known methods, such as with an antibody to the affinity molecule.

The ability of various types of affinity molecules (such as antibodies to different epitopes of the target protein) to facilitate targeting of the recombinant retrovirus and gene delivery can be compared and the molecule with the most desirable characteristics can be selected. Desirable characteristics include, for example, the ability to stimulate efficient endocytosis of the virus, the ability to bind the target molecule with specificity and, similarly, the ability to facilitate binding of the recombinant virus to the target cell. For example, the same target bound by different affinity molecules can be endocytosed differently. Thus, in some embodiments, an affinity molecule with the ability to trigger endocytosis while maintaining binding specificity for a particular target cell type is selected. Similarly, the same antibody-antigen pair could stimulate different endocytosis pathways in different cells, leading to a different ability to facilitate delivery of the gene of interest in the different cells. The assays discussed above with respect to the fusogenic molecule can be modified to compare the abilities of various antibodies, or other affinity molecules, to mediate delivery of a gene of interest to a particular target cell.

The transduction efficiency mediated by different affinity molecules, for example, different anti-CD20 antibodies in different cells, can readily be tested. Transduction can be performed in cells most closely resembling the target cells (or the target cells if available) and efficiency of viral entry quantified and compared. The above BalM-Vpr-based assay and PCR-based assay may be employed to measure the efficiency of viral entry for the different affinity molecules in different cell lines. Furthermore, confocal microscopy can be utilized to investigate the endocytosis induced by different affinity molecules and in different cell types. These detailed studies can assist in determining correlation between transduction efficiency and endocytosis behavior, which can be used to optimize targeting schemes.

Antibodies as Affinity Molecules

In some embodiments the cell-specific binding determinant is an antibody. Antibodies may be generated against any desired cell surface molecule on target cells using well known methods. Antibodies may be generated in an appropriate species to minimize immune response. In other embodiments humanized or chimeric antibodies are prepared and used. For example, antibodies may be generated in a mouse, rabbit or other animal and the variable regions combined with the constant regions of a human antibody. In addition, many antibodies are commercially available and can be selected based on the target molecule on the target cells.

The cell-specific binding determinant is preferably membrane bound or otherwise associated with the membrane of the packaging cell and ultimately the envelope of the recombinant virus. Thus, when the affinity molecule is a soluble antibody it may be necessary to modify the antibody to cause it to associate with the membrane.

In some preferred embodiments, an antibody used as an affinity molecule preferably includes variable regions from an antibody to the target and constant regions from human $IgG_1$ That is, the variable regions of an antibody to the target, such as a soluble antibody are combined with the constant regions of $IgG_1$ to make a membrane bound chimeric immunoglobulin with the desired specificity. If the recombinant retrovirus is to be used in humans, the $IgG_1$ is preferably human. Methods for preparing chimeric antibodies are well known in the art.

In such embodiments the packaging cell (used to assemble the virus) is preferably cotransfected with vectors encoding both the heavy and light chains of $IgG_1$ along with vectors for the expression of immunoglobulin alpha (Igα) and immunoglobulin beta (Igβ). Immunoglobulin alpha (Igα) and immunoglobulin beta (Igβ) help to bind the antibody to the surface membrane of the virus. In some embodiments the antibody is generated in a species other than human, such as mouse or rabbit, and the variable regions are cloned into human $IgG_1$.

In some embodiments, a multicistronic vector is used to direct expression of an antibody and Igα and Igβ. Assembly PCR may be employed to link the antibody heavy chain, light chain, and Igα and Igβ. In one embodiment the genes encoding the three components are separated by three 2A peptides, to facilitate expression from a single promoter. Then, the entire cassette can be cloned into an expression vector such as pcDNA3 (Invitrogen). The efficiency of antibody expression on the surface of packaging cells can be analyzed by FACS staining.

In other embodiments, the affinity molecule is a single chain antibody, either natural or chimeric, and is preferably fused with a transmembrane domain from another protein (Chou et. al., Biotechnol. Bioeng., 65, 160 (1999); Liao et al, Biotechnol. Bioeng., 73, 313 (2001); de Ines et al, J. Immunol., 163, 3948 (1999); Lee et al, J. Immunol., 173, 4618 (2004)). A single chain membrane-bound form of antibody (scAbm) is advantageous in simplifying viral production because display of the natural form of an antibody on the cell surface requires co-expression of four genes: antibody heavy chain, antibody light chain, Igα and Igβ.

scAbms are typically designed to have heavy chain and light chain variable domains linked by a flexible peptide linker. They also carry a signal peptide at their N terminus and a transmembrane domain at their C terminus for anchoring to the cell surface. In some embodiments a slightly different version of scAbm is used, comprising heavy chain and light chain variable domains of the desired antibody (specific to an antigen on the target cell surface) linked by a peptide such as the $(GGGGSGGGS)_2$ peptide, and a dimerization region including the hinge CH2-CH3 domain of human IgG1, and the transmembrane domain and the cytoplasmic tail of the human HLA-A2 to display this chimeric protein on the cell surface.

Thus, in some embodiments a target molecule is identified that is expressed, preferably exclusively or predominantly, on a desired target cell or cell population. Antibodies to the target molecule are generated using standard methods and the variable regions are combined with the constant regions of human $IgG_1$ to form an affinity molecule to direct the recombinant retrovirus to the target cells with specificity.

Non-Antibody Affinity Molecules

In other embodiments, the affinity molecule can be a ligand, preferably a peptide or protein ligand, that binds to a cell surface receptor on a target cell, a receptor that binds to a cell-surface ligand on a target cell. When the affinity molecule is a soluble ligand or receptor, the affinity molecule is preferably constructed as a fusion with a transmembrane domain or other component to anchor it to the membrane. Suitable ligands include, for example, hormones, growth factors, and the like. One specific example of a non-antibody affinity molecule is stem cell factor.

While the affinity molecule can be a naturally occurring molecule, it can also be a non-natural protein, for example, one specifically created to bind to a particular protein on a target cell. In addition, the affinity molecule is not limited to proteins, but could comprise any compound that is able to specifically interact with a molecule on the target cell in such a way as to allow endocytosis of the viral particle into the target cell. For example, in some embodiments the affinity molecule may comprise a carbohydrate.

Delivery Vectors

In a preferred embodiment, one or more vectors are used to introduce the desired polynucleotides into the target cell. The vectors comprise the polynucleotide sequences encoding the various components of the recombinant retrovirus itself, the gene(s) of interest, the fusogenic molecule and affinity molecule, and any components necessary for the production of the virus that are not provided by the packaging cell. These polynucleotides are typically under the control of one or more regulatory elements that direct the expression of the coding sequences in the packaging cell and the target cell, as appropriate. Eukaryotic cell expression vectors are well known in the art and are available from a number of commercial sources.

In some embodiments, packaging cells are transfected with a viral vector (as discussed below) along with two or more additional vectors. For example, in addition to the viral vector a second vector preferably carries a gene encoding a fusogenic molecule, such as HAmu or SINmu, as described elsewhere in the application. A third vector preferably carries a gene encoding an affinity molecule, such as an antibody, as described elsewhere in the application. Furthermore, in some embodiments, one or more additional vectors preferably include genes encoding packaging cell requirements, for example, viral envelope proteins such as pol, env, and gag. Also, in some embodiments, such as where the affinity molecule is an $IgG_1$ immunoglobulin, one or more further vectors are used that encode accessory proteins, such as genes encoding $Ig\alpha$ and $Ig\beta$.

In other embodiments, one or more multicistronic expression vectors are utilized that include two or more of the elements (e.g., the viral genes, gene(s) of interest, the FM, affinity molecule, $Ig\alpha$, $Ig\beta$) necessary for production of the desired recombinant retrovirus in packaging cells. The use of multicistronic vectors reduces the total number of vectors required and thus avoids the possible difficulties associated with coordinating expression from multiple vectors. In a multicistronic vector the various elements to be expressed are operably linked to one or more promoters (and other expression control elements as necessary). For example, in one embodiment a multicistronic expression vector is used to express an antibody affinity molecule and associated components. The vector preferably comprises polynucleotides encoding the antibody heavy and light chain and $Ig\alpha$ and $Ig\beta$. In other embodiments a multicistronic vector comprising a gene of interest, a reporter gene, and viral elements is used. Such a vector may be cotransfected, for example, along with a multicistronic vector encoding both the FM and affinity molecules.

Each component to be expressed in a multicistronic expression vector may be separated by a an IRES element or a viral 2A element to allow for separate expression of the various proteins from the same promoter. IRES elements and 2A elements are known in the art (U.S. Pat. No. 4,937,190; de Felipe et al. Traffic 5:616-626 (2004)). In one embodiment, oligonucleotides encoding furin cleavage site sequences (RAKR) (Fang et al. Nat. Biotech 23, 584-590 (2005)) linked with 2A-like sequences from foot-and-mouth diseases virus (FMDV), equine rhinitis A virus (ERAV), and thosea asigna virus (TaV) (Szymczak et al. (2004) Nat. Biotechnol. 22, 589-594) are used to separate genetic elements in a multicistronic vector. The efficacy of a particular multicistronic vector for use in synthesizing the desired recombinant retrovirus can readily be tested by detecting expression of each of the genes using standard protocols.

Generation of the vector(s) can be accomplished using any suitable genetic engineering techniques known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

The vector(s) may incorporate sequences from the genome of any known organism. The sequences may be incorporated in their native form or may be modified in any way. For example, the sequences may comprise insertions, deletions or substitutions.

Expression control elements that may be used for regulating the expression of the components are known in the art and include, but are not limited to, inducible promoters, constitutive promoters, secretion signals, enhancers and other regulatory elements.

In one embodiment, a vector will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

The vector(s) may include one or more genes for selectable markers that are effective in a eukaryotic cell, such as a gene for a drug resistance selection marker. This gene encodes a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g., ampicillin, neomycin, methotrexate, or tetracycline, complement auxotrophic deficiencies, or supply critical nutrients withheld from the media. The selectable marker can optionally be present on a separate plasmid and introduced by co-transfection.

Vectors will usually contain a promoter that is recognized by the packaging cell and that is operably linked to the polynucleotide(s) encoding the FM, affinity molecule, viral components, and the like. A promoter is an expression control element formed by a DNA sequence that permits binding of RNA polymerase and transcription to occur. Promoters are untranslated sequences that are located upstream (5') to the start codon of a structural gene (generally within about 100 to 1000 bp) and control the transcription and translation of the antigen-specific polynucleotide sequence to which they are operably linked. Promoters may be inducible or constitutive. Inducible promoters initiate increased levels of transcription from DNA under their control in response to some change in culture conditions, such as a change in temperature.

One of skill in the art will be able to select an appropriate promoter based on the specific circumstances. Many different promoters are well known in the art, as are methods for operably linking the promoter to the gene to be expressed. Both native promoter sequences and many heterologous promoters may be used to direct expression in the packaging cell and target cell. However, heterologous promoters are preferred, as they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system.

Transcription may be increased by inserting an enhancer sequence into the vector(s). Enhancers are typically cis-acting elements of DNA, usually about 10 to 300 bp in length, that act on a promoter to increase its transcription. Many enhancer sequences are now known from mammalian genes (globin, elastase, albumin, α-fetoprotein, and insulin). Preferably an enhancer from a eukaryotic cell virus will be used. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors will also contain sequences necessary for the termination of transcription and for stabilizing the mRNA. These sequences are often found in the 5' and, occasionally 3', untranslated regions of eukaryotic or viral DNAs or cDNAs and are well known in the art.

Plasmid vectors containing one or more of the components described above are readily constructed using standard techniques well known in the art.

For analysis to confirm correct sequences in plasmids constructed, the plasmid may be replicated in *E. coli*, purified, and analyzed by restriction endonuclease digestion, and/or sequenced by conventional methods.

Vectors that provide for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the antigen-specific polynucleotide in the expression vector. Sambrook et al., supra, pp. 16.17-16.22.

Other vectors and methods suitable for adaptation to the expression of the viral polypeptides are well known in the art and are readily adapted to the specific circumstances.

Using the teachings provided herein, one of skill in the art will recognize that the efficacy of a particular expression system can be tested by transforming packaging cells with a vector comprising a gene encoding a reporter protein and measuring the expression using a suitable technique, for example, measuring fluorescence from a green fluorescent protein conjugate. Suitable reporter genes are well known in the art.

Transformation of packaging cells with vectors of the present invention is accomplished by well-known methods, and the method to be used is not limited in any way. A number of non-viral delivery systems are known in the art, including for example, electroporation, lipid-based delivery systems including liposomes, delivery of "naked" DNA, and delivery using polycyclodextrin compounds, such as those described in Schatzlein A G. 2001. Non-Viral Vectors in Cancer Gene Therapy: Principles and Progresses. *Anticancer Drugs*. Cationic lipid or salt treatment methods are typically employed, see, for example, Graham et al. Virol. 52:456, (1973); Wigler et al. Proc. Natl. Acad. Sci. USA 76:1373-76, (1979). The calcium phosphate precipitation method is preferred. However, other methods for introducing the vector into cells may also be used, including nuclear microinjection and bacterial protoplast fusion.

Viral Vector and Packaging Cells

One of the vectors encodes the core virus (the "viral vector"). There are a large number of available viral vectors that are suitable for use with the invention, including those identified for human gene therapy applications, such as those described in Pfeifer A, Verma I M. 2001. Gene Therapy: promises and problems. *Annu. Rev. Genomics Hum. Genet.* 2:177-211. Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. Human Immunodeficiency virus (HIV-1)-derived vectors belong to this category. Other examples include lentivirus vectors derived from HIV-2, feline immunodeficiency virus (FIV), equine infectious anemia virus, simian immunodeficiency virus (SIV) and maedi/visna virus.

The viral vector preferably comprises one or more genes encoding components of the recombinant virus as well as one or more genes of interest. The viral vector may also comprise genetic elements that facilitate expression of the gene of interest in a target cell, such as promoter and enhancer sequences. In order to prevent replication in the target cell, endogenous viral genes required for replication may be removed and provided separately in the packaging cell line.

In a preferred embodiment the viral vector comprises an intact retroviral 5' LTR and a self-inactivating 3' LTR.

Any method known in the art may be used to produce infectious retroviral particles whose genome comprises an RNA copy of the viral vector. To this end, the viral vector (along with other vectors encoding the FM, affinity molecule, etc.) is preferably introduced into a packaging cell line that packages viral genomic RNA based on the viral vector into viral particles.

The packaging cell line provides the viral proteins that are required in trans for the packaging of the viral genomic RNA into viral particles. The packaging cell line may be any cell line that is capable of expressing retroviral proteins. Preferred packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430). The packaging cell line may stably express the necessary viral proteins. Such a packaging cell line is described, for example, in U.S. Pat. No. 6,218,181. Alternatively a packaging cell line may be transiently transfected with plasmids comprising nucleic acid that encodes one or more necessary viral proteins (along with the viral vector and the vectors encoding the FM and affinity molecules).

Viral particles comprising a polynucleotide with the gene of interest and an envelope comprising the FM and affinity molecules are collected and allowed to infect the target cell. Target cell specificity may be further improved by pseudotyping the virus. Methods for pseudotyping are well known in the art.

In one embodiment, the recombinant retrovirus used to deliver the gene of interest is a modified lentivirus and the viral vector is based on a lentivirus. As lentiviruses are able to infect both dividing and non-dividing cells, in this embodiment it is not necessary for target cells to be dividing (or to stimulate the target cells to divide).

In another embodiment the vector is based on the murine stem cell virus (MSCV). The MSCV vector provides long-term stable expression in target cells, particularly hematopoietic precursor cells and their differentiated progeny.

In another embodiment, the vector is based on a modified Moloney virus, for example a Moloney Murine Leukemia Virus. In a further embodiment, the vector is based on a Murine Stem Cell Virus (Hawley, R. G., et al. (1996) Proc. Natl. Acad. Sci. USA 93:10297-10302; Keller, G., et al. (1998) Blood 92:877-887; Hawley, R. G., et al. (1994) Gene Ther. 1:136-138). The viral vector can also can be based on a hybrid virus such as that described in Choi, J K; Hoanga, N; Vilardi, A M; Conrad, P; Emerson, S G; Gewirtz, A M. (2001) *Stem Cells* 19, No. 3, 236-246.

A DNA viral vector may be used, including, for example adenovirus-based vectors and adeno-associated virus (AAV)-based vectors. Likewise, retroviral-adenoviral vectors also can be used with the methods of the invention.

Other vectors also can be used for polynucleotide delivery including vectors derived from herpes simplex viruses (HSVs), including amplicon vectors, replication-defective HSV and attenuated HSV (Krisky D M, Marconi P C, Oligino T J, Rouse R J, Fink D J, et al. 1998. Development of herpes simplex virus replication-defective multigene vectors for combination gene therapy applications. *Gene Ther.* 5: 1517-30).

Other vectors that have recently been developed for gene therapy uses can also be used with the methods of the invention. Such vectors include those derived from baculoviruses and alpha-viruses. (Jolly D J. 1999. Emerging viral vectors. pp 209-40 in Friedmann T, ed. 1999. The development of human gene therapy. New York: Cold Spring Harbor Lab).

In the preferred embodiments the viral construct comprises sequences from a lentivirus genome, such as the HIV genome or the SIV genome. The viral construct preferably comprises sequences from the 5' and 3' LTRs of a lentivirus. More preferably the viral construct comprises the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Preferably the LTR sequences are HIV LTR sequences.

The viral construct preferably comprises an inactivated or self-inactivating 3' LTR. The 3' LTR may be made self-inactivating by any method known in the art. In the preferred embodiment the U3 element of the 3' LTR contains a deletion of its enhancer sequence, preferably the TATA box, Spl and NF-kappa B sites. As a result of the self-inactivating 3' LTR, the provirus that is integrated into the host cell genome will comprise an inactivated 5' LTR.

Optionally, the U3 sequence from the lentiviral 5' LTR may be replaced with a promoter sequence in the viral construct. This may increase the titer of virus recovered from the packaging cell line. An enhancer sequence may also be included. Any enhancer/promoter combination that increases expression of the viral RNA genome in the packaging cell line may be used. In a preferred embodiment the CMV enhancer/promoter sequence is used.

The viral construct generally comprises a gene that encodes a protein (or other molecule, such as siRNA) that is desirably expressed in one or more target cells. Preferably the gene of interest is located between the 5' LTR and 3' LTR sequences. Further, the gene of interest is preferably in a functional relationship with other genetic elements, for example transcription regulatory sequences such as promoters and/or enhancers, to regulate expression of the gene of interest in a particular manner once the gene is incorporated into the target cell. In certain embodiments, the useful transcriptional regulatory sequences are those that are highly regulated with respect to activity, both temporally and spatially.

Preferably the gene of interest is in a functional relationship with internal promoter/enhancer regulatory sequences. An "internal" promoter/enhancer is one that is located between the 5' LTR and the 3' LTR sequences in the viral construct and is operably linked to the gene that is desirably expressed.

The internal promoter/enhancer may be any promoter, enhancer or promoter/enhancer combination known to increase expression of a gene with which it is in a functional relationship. A "functional relationship" and "operably linked" mean, without limitation, that the gene is in the correct location and orientation with respect to the promoter and/or enhancer that expression of the gene will be affected when the promoter and/or enhancer is contacted with the appropriate molecules.

The internal promoter/enhancer is preferably selected based on the desired expression pattern of the gene of interest and the specific properties of known promoters/enhancers. Thus, the internal promoter may be a constitutive promoter. Non-limiting examples of constitutive promoters that may be used include the promoter for ubiquitin, CMV (Karasuyama et al J. Exp. Med. 169:13 (1989), beta-actin (Gunning et al. Proc. Natl. Acad. Sci. USA 84:4831-4835 (1987) and pgk (see, for example, Adra et al. Gene 60:65-74 (1987), Singer-Sam et al. Gene 32:409-417 (1984) and Dobson et al. Nucleic Acids Res. 10:2635-2637 (1982)).

Alternatively, the promoter may be a tissue specific promoter. Several non-limiting examples of tissue specific promoters that may be used include lck (see, for example, Garvin et al. Mol. Cell. Biol. 8:3058-3064 (1988) and Takadera et al. Mol. Cell. Biol. 9:2173-2180 (1989)), myogenin (Yee et al. Genes and Development 7:1277-1289 (1993), and thy1 (Gundersen et al. Gene 113:207-214 (1992). In addition, promoters may be selected to allow for inducible expression of the gene. A number of systems for inducible expression are known in the art, including the tetracycline responsive system and the lac operator-repressor system. It is also contemplated that a combination of promoters may be used to obtain the desired expression of the gene of interest. The skilled artisan will be able to select a promoter based on the desired expression pattern of the gene in the organism and/or the target cell of interest.

In some embodiments the viral construct preferably comprises at least one RNA Polymerase II or III promoters. The RNA Polymerase II or III promoter is operably linked to the gene of interest and can also be linked to a termination sequence. In addition, more than one RNA Polymerase II or III promoters may be incorporated.

RNA polymerase II and III promoters are well known to one of skill in the art. A suitable range of RNA polymerase III promoters can be found, for example, in Paule and White. *Nucleic Acids Research.*, *Vol* 28, pp 1283-1298 (2000), which is hereby incorporated by reference in its entirety. The definition of RNA polymerase II or III promoters, respectively, also include any synthetic or engineered DNA fragment that can direct RNA polymerase II or III, respectively, to transcribe its downstream RNA coding sequences. Further, the RNA polymerase II or III (Pol II or III) promoter or promoters used as part of the viral vector can be inducible. Any suitable inducible Pol II or III promoter can be used with the methods of the invention. Particularly suited Pol II or III promoters include the tetracycline responsive promoters provided in Ohkawa and Taira *Human Gene Therapy*, Vol. 11, pp 577-585 (2000) and in Meissner et al. *Nucleic Acids Research*, Vol. 29, pp 1672-1682 (2001), which are incorporated herein by reference.

An internal enhancer may also be present in the viral construct to increase expression of the gene of interest. For example the CMV enhancer (Karasuyama et al J. Exp. Med. 169:13 (1989) may be used in combination with the chicken .beta.-actin promoter. Again, one of skill in the art will be able to select the appropriate enhancer based on the desired expression pattern.

The gene of interest is not limited in any way and includes any nucleic acid that the skilled practitioner desires to have integrated, transcribed, translated, and/or expressed in the target cell. For example, the gene of interest may encode a polypeptide, such as a hormone, toxin or antigen, or encode a nucleotide such as an siRNA.

In some embodiments, a gene of interest is incorporated as a safety measure and allows for the selective killing of infected target cells within a heterogeneous population, for example within an animal, such as within a human patient. In one such embodiment, the gene of interest is a thymidine kinase gene (TK), the expression of which renders a target cell susceptible to the action of the drug gancyclovir.

In addition, more than one gene of interest may be placed in functional relationship with the internal promoter. For example a gene encoding a marker protein may be placed after the primary gene of interest to allow for identification of cells that are expressing the desired protein. In one embodiment a fluorescent marker protein, preferably green fluorescent protein (GFP), is incorporated into the construct along with the gene of interest. If one or more additional reporter genes is included, internal ribosomal entry site (IRES) sequences, or 2A elements are also preferably included, separating the primary gene of interest from a reporter gene and/or any other gene of interest. The IRES or 2A sequences may facilitate the expression of the reporter gene, or other genes.

The viral construct may also contain additional genetic elements. The types of elements that may be included in the construct are not limited in any way and will be chosen by the skilled practitioner to achieve a particular result. For example, a signal that facilitates nuclear entry of the viral genome in the target cell may be included. An example of such a signal is the HIV-1 flap signal.

Further, elements may be included that facilitate the characterization of the provirus integration site in the target cell. For example, a tRNA amber suppressor sequence may be included in the construct.

In addition, the construct may contain one or more genetic elements designed to enhance expression of the gene of interest. For example, a woodchuck hepatitis virus responsive element (WRE) may be placed into the construct (Zufferey et al. J. Virol. 74:3668-3681 (1999); Deglon et al. Hum. Gene Ther. 11:179-190 (2000)).

A chicken .beta.-globin insulator may also be included in the viral construct. This element has been shown to reduce the chance of silencing the integrated provirus in the target cell due to methylation and heterochromatinization effects. In addition, the insulator may shield the internal enhancer, promoter and exogenous gene from positive or negative positional effects from surrounding DNA at the integration site on the chromosome.

Any additional genetic elements are preferably inserted 3' of the gene of interest.

In a specific embodiment, the viral vector comprises: a cytomegalovirus (CMV) enhancer/promoter sequence; the R and U5 sequences from the HIV 5' LTR; the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken beta-globin insulator; and the R and U5 sequences of the 3' HIV LTR.

The viral construct is preferably cloned into a plasmid that may be transfected into a packaging cell line. The preferred plasmid preferably comprises sequences useful for replication of the plasmid in bacteria.

Delivery of the Virus

The virus may be delivered to the cell in any way that allows the virus to contact the target cells in which delivery of the gene of interest is desired. In preferred embodiments, a suitable amount of virus is introduced into an animal directly (in vivo), for example though injection into the body. In one such embodiment, the viral particles are injected into the animal's peripheral blood stream. Other injection locations also are suitable, such as directly into organs comprising target cells. For example intracranial or intrahepatic injection may be used to deliver virus to the brain and liver respectively. Depending on the particular circumstances and nature of the target cells, introduction can be carried out through other means including for example, inhalation, or direct contact with epithelial tissues, for example those in the eye, mouth or skin.

In other embodiments, target cells are preferably contacted with the virus in vitro, such as in culture plates. The virus may be suspended in media and added to the wells of a culture plate, tube or other container. The media containing the virus may be added prior to the plating of the cells or after the cells have been plated. Preferably cells are incubated in an appropriate amount of media to provide viability and to allow for suitable concentrations of virus in the media such that infection of the host cell occurs.

The cells are preferably incubated with the virus for a sufficient amount of time to allow the virus to infect the cells. Preferably the cells are incubated with virus for at least 1 hour, more preferably at least 5 hours and even more preferably at least 10 hours.

In both in vivo and in vitro delivery embodiments, any concentration of virus that is sufficient to infect the desired target cells may be used, as can be readily determined by the skilled artisan. When the target cell is to be cultured, the concentration of the viral particles is at least 1 pfu/µl, more preferably at least 10 pfu/µl, even more preferably at least 400 pfu/µl and even more preferably at least $1 \times 10^4$ pfu/µl.

In some embodiments, following infection with the virus in vitro, target cells can be introduced into an animal. The location of introduction of cultured cells will depend on the cell type used and the desired effect. For example, when the cells are hematopoietic cells, the cells can be introduced into the peripheral blood stream. The cells introduced into an animal are preferably cells derived from that animal, to avoid an adverse immune response. Cells also can be used that are derived from a donor animal having a similar immune makeup. Other cells also can be used, including those designed to avoid an immunogenic response.

The cells and animals incorporating target cells may be analyzed, for example for integration, transcription and/or expression of the gene(s) of interest, the number of copies of the gene integrated, and the location of the integration. Such analysis may be carried out at any time and may be carried out by any methods known in the art.

The methods of infecting cells disclosed above do not depend upon species-specific characteristics of the cells. As a result, they are readily extended to all mammalian species. In some embodiments the recombinant virus is delivered to a human or to human cells. In other embodiments it is delivered to an animal other than a human or non-human cells.

As discussed above, the modified retrovirus can be pseudotyped to confer upon it a broad host range. One of skill in the art would also be aware of appropriate internal promoters to achieve the desired expression of a gene of interest in a particular animal species. Thus, one of skill in the art will be able to modify the method of infecting cells derived from any species.

Target Cells

A wide variety of cells may be targeted in order to deliver a gene of interest using a recombinant retrovirus as disclosed herein. The target cells will generally be chosen based upon the gene of interest and the desired effect.

In some embodiments, a gene of interest may be delivered to enable a target cell to produce a protein that makes up for a deficiency in an organism, such as an enzymatic deficiency, or immune deficiency, such as X-linked severe combined immunodeficiency. Thus, in some embodiments, cells that would normally produce the protein in the animal are targeted. In other embodiments, cells in the area in which a protein would be most beneficial are targeted.

In other embodiments, a gene of interest, such as a gene encoding an siRNA, may inhibit expression of a particular gene in a target cell. The gene of interest may, for example, inhibit expression of a gene involved in a pathogen life cycle. Thus cells susceptible to infection from the pathogen or infected with the pathogen may be targeted. In other embodiments, a gene of interest may inhibit expression of a gene that is responsible for production of a toxin in a target cell.

In other embodiments a gene of interest may encode a toxic protein that kills cells in which it is expressed. In this case, tumor cells or other unwanted cells may be targeted.

In still other embodiments a gene that encodes a protein to be collected, such as a therapeutic protein may be used and cells that are able to produce and secrete the protein are targeted.

Once a particular population of target cells is identified in which expression of a gene of interest is desired, a target molecule is selected that is specifically expressed on that population of target cells. The target molecule may be expressed exclusively on that population of cells or to a greater extent on that population of cells than on other populations of cells. The more specific the expression, the more specifically gene delivery can be directed to the target cells. Depending on the context, the desired amount of specificity of the marker (and thus of the gene delivery) may vary. For example, for introduction of a toxic gene, a high specificity is most preferred to avoid killing non-targeted cells. For expression of a protein for harvest, or expression of a secreted product where a global impact is desired, less marker specificity may be needed.

As discussed above, the target molecule may be any molecule for which a specific binding partner can be identified or created. Preferably the target molecule is a peptide or polypeptide, such as a receptor. However, in other embodiments the target molecule may be a carbohydrate or other molecule that can be recognized by a binding partner. If a binding partner for the target molecule is already known, it may be used as the affinity molecule. However, if a binding molecule is not known, antibodies to the target molecule may be generated using standard procedures. The antibodies can then be used as the affinity molecule, or to create an affinity molecule.

Thus, target cells may be chosen based on a variety of factors, including, for example, (1) the particular application (e.g., therapy, expression of a protein to be collected, and conferring disease resistance) and (2) expression of a marker with the desired amount of specificity.

Target cells are not limited in any way and include both germline cells and cell lines and somatic cells and cell lines. Target cells can be stem cells derived from either origin. When the target cells are germline cells, the target cells are preferably selected from the group consisting of single-cell embryos and embryonic stem cells (ES).

In one embodiment, target cells are CD20+ cell (see Examples 1-5). Some other non-limiting examples of target cells are CD34+ cells, CD4+ cells, dendritic cells, tumor cells and other dysfunctional cells, and cells that are susceptible to infection with a pathogen. Various affinity molecules are available to target numerous cell types, for example, CD34+ cells, and dendritic cells, described in more detail below.

Depending on the vector that is to be used, target cell division may be required for transformation. Target cells can be stimulated to divide in vitro by any method known in the art. For example, hematopoietic stem cells can be cultured in the presence of one or more growth factors, such as IL-3, IL-6 and/or stem cell factor (SCF).

Although examples are discussed below in relation to the targeting CD34+ stem cells and dendritic cells, one of skill in the art will be able to adapt the disclosure to other contexts.

Targeting of Lentiviral Vectors to Human $CD34^+$ Hematopoietic Stem Cells

CD34 is a human hematopoietic stem cell (HSC) marker. HSCs may be programmed to differentiate into antigen-specific immune cells via virus-mediated gene transfer. Targeted gene delivery into $CD34^+$ HSC allows gene transfer in vivo, but could also be used in vitro. Therefore, a wide range of hematological disorders, such as various anemias, leukemias, lymphomas, and platelet disorders may be treated using the disclosed methods and vectors to deliver the appropriate polynucleotides to HSCs. Polynucleotides encoding proteins whose expression in HSCs would be beneficial to treatment of the various hematological disorders will be apparent to the skilled artisan.

In some embodiments of the invention, CD34 is targeted. Various examples of anti-CD34 antibodies are available and can be used as the basis of an affinity molecule or as the affinity molecule if they are membrane associated. For example, ATCC number HB-12346 is readily available from the ATCC and can be used to prepare an affinity molecule. Evaluation of the functional expression of anti-CD34 antibodies as the affinity molecule on recombinant retrovirus may be accomplished using a virus-cell binding assay. TF-1a, a human CD34+ cell line, may be obtained from the ATCC (ATCC number: CRL-2451) and used as a target cell for such binding experiments. Transduction experiments may then be conducted in the TF-1a line and primary human bone marrow or cord blood cells. Transduction efficiency may be compared between various antibodies, including natural and single chain forms. Once an efficient affinity molecule is identified, it can be used in conjunction with an FM, such as SINmu or HAmu, to deliver a gene of interest to CD34+ cells, either in vivo or in vitro.

Targeting of Recombinant Virus to Dendritic Cells in vivo

Dendritic cells (DCs) have been widely used to induce tumor-specific killer (CD8) and helper (CD4) T cell responses in animal-tumor models and in cancer patients (Schuler et al. Curr. Top. Microbiol. 281, 137-178 (2003)). Targeting of antigens and the induction of their maturation are part of an in situ DC vaccination approach. Thus, targeting lentiviral vectors to DCs in vivo using viruses as described herein can be used therapeutically, for example, in treating melanoma and HIV. The DEC-205 endocytosis receptor is a preferred target surface antigen on the DC as DEC-205 is abundantly expressed on lymphoid tissue and can significantly improve the efficiency of antigen presentation. (Bonifaz, L. C. et al. J. Exp. Med. 199, 815-824 (2004)). Anti-DEC-205 antibody, preferably comprising the variable regions from an anti-DEC205 antibody with the constant regions of IgG1) can be displayed on the surface of a viral particle as the affinity molecule to direct co-delivery of both a gene encoding an antigenic protein and a maturation stimulatory molecule, such as TNFα or CD40L, into DCs. A maturation signal could also be delivered along with an antigen gene by using anti-CD40 antibody as an affinity molecule.

As described in Example 6 below, recombinant lentiviruses have been created that co-display αmDEC-205 and SINmu to target bone marrow derived DCs in vitro. To target human DCs, membrane-bound antibodies against human DCs, such as $IgG_1$ comprising the variable region from a human anti-DEC-205 antibody, are engineered into recombinant viruses Diseases such as HIV and melanoma can then be prevented and/or treated by delivery of appropriate antigen genes to DCs using the recombinant virus. In one embodiment, an anti-DEC-205 antibody comprising the variable regions from a murine anti-DEC-205 antibody and the constant regions from human $IgG_1$ is used as an affinity molecule and SINmu is used as a fusogenic molecule (see Example 6) to target a recombinant lentivirus to DCs and deliver a gene encoding an antigen.

Transgenic Animals

The methods of the present invention can be used to create transgenic animals. In some embodiments particular cells in an adult animal are targeted to deliver a polynucleotide encoding a gene to be expressed in those cells. In other embodiments an oocyte or one or more embryonic cells are infected with recombinant virus produced as described above. The virus delivers a polynucleotide encoding a gene of interest that is incorporated into the genome of the developing animal and can be transmitted from generation to generation. One of skill in the art will recognize that the method of infection and the treatment of the cell following infection will depend upon the type of animal from which the cell is obtained, and that the ability to target gene delivery to particular cell types allows for in vivo or in vitro gene delivery.

Therapy

The methods of the present invention can be used to prevent or treat a wide variety of diseases or disorders. Diseases or disorders that are amenable to treatment or prevention by the methods of the present invention include, without limitation, cancers, autoimmune diseases, and infections, including viral, bacterial, fungal and parasitic infections. In some embodiments a disease is treated by using recombinant retroviruses to deliver a gene of interest to target cells, wherein expression of the gene produces a protein or other molecule that addresses a deficiency in the cell or in the animal as a whole.

In other embodiments, a gene is delivered to the target cell type that regulates expression of a protein that is involved in the disease or disorder. For example, a gene encoding an siRNA molecule may be provided to inhibit a gene involved in a pathogen life cycle, to reduce the expression of a protein that is being overproduced, or to interfere with a pathway involved in the progression of the disease or disorder. In other examples, genes are delivered that inhibit a particular cellular activity by competing with a native molecule or that enhance a cellular activity by acting synergistically or facilitating the activity of a native molecule.

In still other embodiments a gene is delivered that causes the death of undesirable target cells, such as tumor cells. Alternatively a gene may be delivered that prevents or reduces the ability of a tumor cell to multiply.

Although illustrated in several particular contexts below, the skilled artisan will be able to adapt the methods and constructs disclosed herein in view of specific circumstances.

siRNAs

The methods described herein allow for vector-mediated delivery of RNA molecules, and are particularly suited to the delivery to and expression of small RNA molecules in target cells. According to some embodiments of the invention, an RNA molecule is delivered to a target cell, and then expressed within the target cell in order to down-regulate the expression of a target gene. The ability to down-regulate a target gene has many therapeutic and research applications, including identifying the biological functions of particular genes. By delivering an RNA molecule to a target cell and subsequently expressing the RNA molecule within the target cell, it is possible to knock-down (or down-regulate) the expression of any of a large number of genes, both in cell culture and in mammalian organisms. In some embodiments genes that are necessary for the life cycle of a pathogen, such as a pathogenic virus, or that are contributing directly or indirectly to a disease or disorder are downregulated in a target cell with siRNA.

Thus, in some embodiments, the viral vector comprises an RNA expression cassette encoding an siRNA molecule. An RNA expression cassette to be delivered to a target cell preferably comprises a Pol III promoter and an RNA coding region. The RNA coding region preferably encodes an RNA molecule that is capable of down-regulating the expression of a particular gene or genes. The RNA molecule encoded can, for example, be complementary to the sequence of an RNA molecule encoding a gene to be down-regulated. In such an embodiment, the RNA molecule is designed to act through an antisense mechanism.

A preferred embodiment involves the delivery to a target cell and subsequent expression of a double-stranded RNA complex, or an RNA molecule having a stem-loop or a so-called "hairpin" structure. As used herein, the term "RNA duplex" refers to the double stranded regions of both the RNA complex and the double-stranded region of the hairpin or stem-lop structure. An RNA coding region can encode a single stranded RNA, two or more complementary single stranded RNAs or a hairpin forming RNA.

Double stranded RNA has been shown to inhibit gene expression of genes having a complementary sequence through a process termed RNA interference or suppression (see, for example, Hammond et al. Nat. Rev. Genet. 2:110-119 (2001)).

According to some embodiments of the invention, the RNA duplex or siRNA corresponding to a region of a gene to be down-regulated is delivered to a target cell using the vectors described, and is then expressed in the target cell. The RNA duplex is substantially identical (typically at least about 80% identical, and more typically at least about 90% identical) in sequence to the sequence of the gene targeted for down regulation. siRNA duplexes are described, for example, in Bummelkamp et al. Science 296:550-553 (2202), Caplen et al. Proc. Natl. Acad. Sci. USA 98:9742-9747 (2001) and Paddison et al. Genes & Devel. 16:948-958 (2002).

The RNA duplex to be delivered to the target cell is generally at least about 15 nucleotides in length and is preferably about 15 to about 30 nucleotides in length. In some organisms, the RNA duplex can be significantly longer. In a more preferred embodiment, the RNA duplex is between about 19 and 22 nucleotides in length. The RNA duplex is most preferably identical to the target nucleotide sequence over the duplex region.

When the target cell gene to be down regulated is in a family of highly conserved genes, the sequence of the duplex region can be chosen with the aid of sequence comparison to target only the desired gene. If there is sufficient identity among a family of homologous genes within an organism, a duplex region can be designed that would down regulate a plurality of genes simultaneously.

The sequence of the RNA coding region, and thus the sequence of the RNA duplex to be delivered to the target cell, preferably is chosen to be complementary to the sequence of a gene whose expression is to be downregulated in a target cell. The degree of down regulation achieved with a given RNA molecule for a given target gene will vary by sequence. One of skill in the art will be able to readily identify an effective sequence. For example, in order to maximize the amount of suppression, a number of sequences can be tested in cell culture prior to treating target cells.

In some embodiments, the target (within the target cell) of the RNA duplex is a sequence that is necessary for the life cycle or replication of a virus, including for example, gene expression of the virus and the expression of a cellular receptor or co-receptor necessary for viral replication. In one embodiment of the invention, the virus to be inhibited is the human immunodeficiency virus (HIV).

In some embodiments, the gene of interest to be delivered to the target cell encodes at least one double stranded RNA having at least 90% homology and preferably identical to a region of at least about 15 to 25 nucleotides in a nucleotide that is important for normal viral replication. For example, the double stranded RNA may have homology to a nucleic acid in a viral genome, a viral gene transcript or in a gene for a patient's target cellular receptor that is necessary for the life cycle of the virus.

In some embodiments, siRNAs are delivered to treat infection such as HIV, Hepatitis A, B, C, D, E, or a wide range of other viral infections. One of skill in the art can target a cellular component, either an RNA or an RNA encoding a cellular protein necessary for a pathogen life cycle, such as a viral life cycle. In a preferred embodiment, the cellular target chosen will not be a protein or RNA that is necessary for normal cell growth and viability. Suitable proteins for disrupting the viral life cycle include, for example, cell surface receptors involved in viral entry, including both primary receptors and secondary receptors, and transcription factors involved in the transcription of a viral genome, proteins involved in integration into a host chromosome, and proteins involved in translational or other regulation of viral gene expression.

A wide variety of molecules are specifically associated with pathogens and can be targeted by the methods disclosed herein. These include a number of cellular proteins that are known to be receptors for viral entry into cells (Baranowski, et al. *Science* 292: 1102-1105). Some cellular receptors that are involved in recognition by viruses are listed below: Adenoviruses: CAR, Integrins, MHC I, Heparan sulfate glycoaminoglycan, Siliac Acid; Cytomegalovirus: Heparan sulfate glycoaminoglycan; Coxsackieviruses: Integrins, ICAM-1, CAR, MHC I; Hepatitis A: murine-like class I integral membrane clycoprotein; Hepatitis C: CD81, Low density lipoprotein receptor; HIV (Retroviridae): CD4, CXCR4, Heparan sulfate glycoaminoglycan; HSV: Heparan sulfate glycoaminoglycan, PVR, HveB, HveC; Influenza Virus: Sialic acid; Measles: CD46, CD55; Poliovirus,: PVR, HveB, HveC; Human papillomavirus: Integrins. One of skill in the art will recognize that the invention is not limited to use with receptors (or other molecules) that are currently known. As new cellular receptors and coreceptors are discovered, the methods of the invention can be applied to such sequences.

In some embodiments of the invention, HIV is particularly targeted and the retroviral construct comprises an RNA coding region that encodes a double stranded molecule having at least 90% homology to the HIV viral RNA genome, an expressed region of the HIV viral genome (for example, to any region of about 19-25 nucleotides in length of the 9-kb transcript of the integrated HIV virus), or any of the variously spliced mRNA transcripts of HIV (Schwartz et al. *J. Virol.* 1990; 64(6): 2519-29). Target regions within the HIV transcripts can be chosen to correspond to any of the viral genes, including, for example, HIV-1 LTR, vif, nef, and rev. In other embodiments, the RNA coding region encodes a double stranded region having at least 90% homology to a receptor or co-receptor of the HIV virus. For example, the primary receptor for HIV entry into T cells is CD4. In a preferred embodiment, the co-receptors CXC chemokine receptor 4 (CXCR4) and CC chemokine receptor 5 (CCR5) are down-regulated according to the methods of the invention. CXCR4 (Feddersppiel et al. Genomics 16:707-712 (1993)) is the major co-receptor for T cell trophic strains of HIV while CCR5 (Mummidi et al. J. Biol. Chem. 272:30662-30671 (1997)) is the major co-receptor for macrophage trophic strains of HIV. Other cellular targets against HIV include the RNA transcripts for proteins involved in the HIV life cycle, including cyclophilin, CRM-1, importin-$\beta$, HP68 (Zimmerman C, et al. Identification of a host protein essential for assembly of immature HIV-1 capsids. *Nature* 415 (6867): 88-92 (2002)) and other as yet unknown cellular factors.

In one particular embodiment, a recombinant retrovirus is used to introduce siRNAs against the HIV-1 co-receptor CCR5 into human peripheral blood T cells. Reducing CCR5 expression by siRNAs provides protection from CCR5-tropic HIV-1 viral infection (Qin et al. (2003). Proc. Natl. Acad. Sci. 100, 183-188). Targeted delivery of such siRNAs to human CD34$^+$ cells may thus reconstitute CD4+ cells that are resistant to HIV-1 infection. Recombinant lentiviruses comprising an affinity molecule that targets CD34, such as an anti-CD 34 antibody, a fusogenic molecule such as SIN or HA, and encoding CCR5-siRNA and, optionally, GFP may be injected intravenously to treat HIV.

Vaccination

As discussed above, various cell-specific binding determinants to surface dendritic cell markers are contemplated for use in producing recombinant retrovirus that delivers a gene encoding an antigen to DCs. For example, a hybridoma cell line for human anti-DEC-205 antibody ($\alpha$hDEC-205) is available from the ATCC (ATCC number: CRL-2460). A gene encoding an antigen against which an immune response is desired, such as for cancer (for example, Mart-1), or another disease/disorder (such as viral infection) may be delivered to DCs using the methods described above. The gene for the antigen may be accompanied by genes encoding stimulatory molecules, such as TNF$\alpha$/CD40L, and/or a reporter molecule, such as GFP using multiple vectors or, preferably, a multicistronic vector system.

In some embodiments of the invention, human DCs are generated from CD34$\alpha$+ human hematopoietic progenitors using an in vitro culture method (e.g., Banchereau et al. Cell 106, 271-274 (2001)). αhDEC-205 and SINmu-bearing viruses are generated comprising a gene encoding an antigen against which an immune response is desired and are used to transduce human DCs. Transduction specificity and efficiency may be quantified by FACS. Maturation of DCs can be characterized by FACS analysis of up-regulation of surface marker such as MHC II.

In other embodiments, virus may be injected in vivo, where it contacts natural DCs and delivers the gene encoding the antigen. At selected intervals, DCs from the recipient's lymphoid organs may be used to measure expression, for example, by observing marker expression, such as GFP. T cells from lymph nodes and spleens of virus-treated recipients may be measured from the magnitude and durability of response to antigen stimulation. Tissue cells other than DCs, such as epithelial cells and lymphoid cells, may be analyzed for the specificity of in vivo gene delivery.

It is widely agreed that the most effective potential method to end the AIDS epidemic (and other viral diseases) is a vaccine. Unfortunately, to date no vaccination method against HIV has successfully passed a phase III trial. Thus, there is an urgent need for novel and effective vaccination strategies. In some embodiments of the invention DC vaccination is used. A gene is cloned encoding a viral protein, such as those described above, into a viral vector. Patients are infected with viruses comprising an affinity molecule that targets DCs, such as αhDEC-205 by injection. In an animal model, molecularly cloned HIV reporter viruses (NFNSZ-r-HSAS, NL-r-HSAS) and clinical isolates may be used to challenge the animals by tail vein injection. Evidence of infection may be monitored over time in splenocytes, lymph nodes, and peripheral blood. PCR for HIV-gag protein and FACS for HAS in the reporter viruses may be used to test for viral integration and replication. Productive in situ DC vaccination may increase resistance to a HIV challenge.

Treatment of Tumors and Other Abnormal Cells

In other embodiments, the disclosed method can be used to treat tumors or other abnormal cell growth. Tumor associated antigens are known for a variety of cancers including, for example, prostate cancer and breast cancer. In some breast cancers, for example, the Her-2 receptor is overexpressed on the surface of cancerous cells. A number of tumor associated antigens have been reviewed (see, for example, Boon T, Cerottini J C, Vandeneynde B, Vanderbruggen P, Vanpel A, Annual Review Of Immunology 12: 337-365, 1994; Renkvist N, Castelli C, Robbins P F, Parmiani G. Cancer Immunology Immunotherapy 50: (1) 3-15 MAR 2001). Thus, in some embodiments an antibody to a known tumor associated antigen is used to prepare an affinity molecule.

In other embodiments, an antigen related to a disease or disorder is identified from the patient to be treated. For example, an antigen associated with a tumor may be identified from the tumor itself by any method known in the art.

Antibodies to tumor associated antigens may be displayed on a viral surface to target delivery of genes of interest into tumor cells. The genes of interest may encode a toxin whose expression kills the target tumor cells. In some embodiments the expression of the toxin is inducible. In other embodiments the gene of interest may interfere with the cell cycle and reduce or eliminate the ability of the cell to divide.

These methods may be adapted to treat a wide range of diseases by selecting a particular target molecule on a pathologic cell of interest and synthesizing an affinity molecule to that particular target molecule. Next, a recombinant retrovirus with the membrane bound affinity molecule and a fusogenic molecule is assembled to deliver the gene of interest into the target cell.

In some embodiments, a recombinant retrovirus may be used to target a non-Hodgkin's lymphoma cell. A HSV thymidine kinase (HSV-tk) suicide gene and a GFP reporter gene may be delivered into tumor cells; these two genes may be linked by an internal ribosome entry site (IRES) to accomplish co-expression.

In some embodiments, a retrovirus as described herein may be used to target a tumor cell with a specific cell surface antigen, such as a breast cancer tumor cell. A hybridoma cell line for anti-human Her2 antibody is available from the ATCC (ATCC number: CRL: 1043). Viruses bearing such antibodies may be used to target and kill cancer cells.

Treatment of X-linked Severe Combined Deficiency

Genetic defects in the common γ chain ($\gamma_c$) result in the X-linked severe combined immunodeficiency disease (X-SCID) in humans. Without treatment, X-SCID patients suffer from severe infections, failure to thrive, and usually die within the first year of life. It is commonly agreed that the ultimate therapeutic treatment for this disease is gene therapy. A retrovirus as disclosed may be used to deliver the common $\gamma_c$ gene into purified CD34$^+$ hematopoietic stem cells (HSCs) in vitro and transfer back $\gamma_c$ transduced HSCs to patients to reconstitute the immune system. In other embodiments, the recombinant virus is provided in vivo and targets CD34+ stem cells to treat X-SCID. SCF can be used to specifically target the recombinant retrovirus to the target cells, where the $\gamma_c$ gene is delivered.

In one embodiment patients suffering from X-SCID are treated. The full length of $\gamma_c$ cDNA is amplified and cloned into a lentiviral vector as described above. Packaging cells, such as 293 cells are transfected with the lentiviral vector, as well as one or more vectors encoding an affinity molecule and a fusogenic molecule. The viruses bearing SCF, or another affinity molecule targeting HSCs and a fusogenic molecule, such as SINmu, are collected and concentrated. The $\gamma_c$ deficient patients are administered the viruses by injection. Testing with and without mobilization may be performed to relocate HSCs to circulating blood. Peripheral lymphoid cells may then be analyzed for 6-8 weeks to detect the existence of mature T and B cells.

Antigen-Specific Immune Cell Therapy

In other embodiments recombinant retrovirus is used to deliver polynucleotides encoding immune cell receptors, such as T Cell receptors or B cell receptors, to human stem cells. The stem cells then develop into mature immune cells, such as T cells or B cells, with their specificity determined by the receptor with which they were transduced. In one embodiment, a patient that is suffering from a disease or disorder is treated by generating immune cells with a desired specificity using this approach. An antigen may be previously known to be associated with the disease or disorder, or may be identified by any method known in the art. For example, an antigen to a type of cancer from which a patient is suffering may be known, such as a tumor associated antigen. Tumor associated antigens are not limited in any way and include, for example, antigens that are identified on cancerous cells from the patient to be treated.

Once an antigen has been identified and/or selected, one or more T cell receptors that are specific for the antigen are then identified. If a T cell receptor specific for the identified disease-associated antigen is not already known, it may be identified by any method known in the art. T cell receptors may be identified from cytotoxic T cells, from helper T cells, or both, depending on the type of immune cell that is to be generated in the patient. For example, if cytotoxic T cells are to be generated in the patient, the T cell receptor is identified from a CTL. On the other hand, if helper T cells are to be generated, the T cell receptor is identified from a helper T cell. As discussed below, in some embodiments a T cell receptor from a CTL and a T cell receptor from a helper T cell are both utilized.

A polynucleotide that encodes the desired T cell receptor is identified. Preferably the polynucleotide comprises a cDNA that encodes the T cell receptor α subunit and a cDNA that encodes the T cell receptor β subunit. The polynucleotides encoding the T cell receptor are preferably introduced into target cells (preferably hematopoietic stem cells) using a modified retrovirus, more preferably a modified lentivirus, including a fusion molecule and cell-specific binding determinant as described above. The virus first binds to the target cell membrane by way of the membrane-bound affinity molecule, and the polynucleotides encoding the T cell receptor subunits enter the cytosol by action of the fusion molecule. The gene of interest (e.g., one encoding the T cell receptor) is then preferably integrated into the cell's genome and expressed. If contacted ex vivo, the target cells are then transferred back to the patient, for example by injection, where they develop into immune cells that are capable of generating an immune response when contacted with the identified antigen. However, in preferred embodiments the virus is injected into the patient where it specifically transduces the targeted cells. The resulting immune cells generated in the patient express the particular TCR and the patient is able to mount an effective immune response against the disease or disorder.

In some embodiments the T cell receptor is cloned from cytotoxic T cells. This results in the generation of cytotoxic T cells in the patient. In other embodiments the T cell receptor is cloned from a helper T cell, resulting in the generation of helper T cells in the patient.

In still other embodiments B cells are generated in the patient by delivering polynucleotides encoding B cell receptors to the target cells. The population of target cells is divided and some stem cells are transfected with a vector encoding a T cell receptor obtained from a cytotoxic T cell and some stem cells are transfected with a vector encoding a T cell receptor obtained from a helper T cell. The target stem cells are transferred into the patient, resulting in the simultaneous generation of a population of helper T cells specific for the disease or disorder and a population of cytotoxic T cells specific for the disease or disorder in the patient.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patent and literature references cited in the present specification are hereby incorporated by reference in their entirety.

EXPERIMENTAL METHODS

Figure 13:
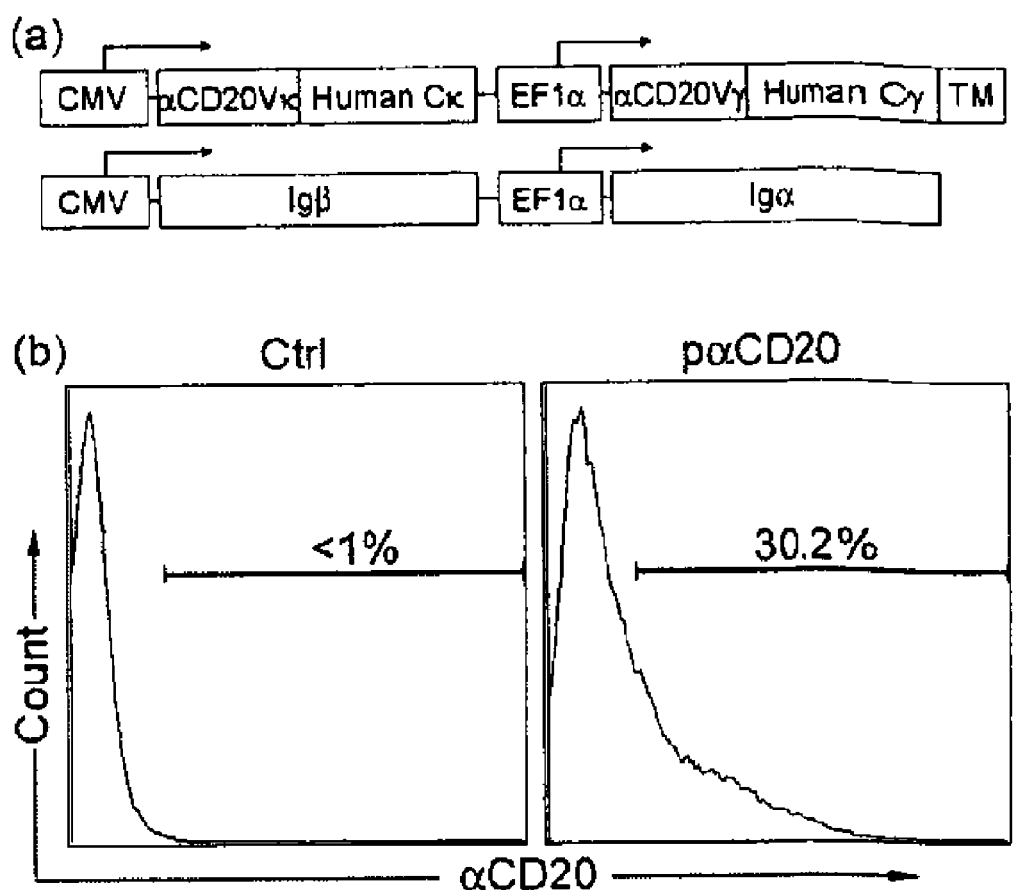
FIG. 13a shows constructs for expression of membrane-bound αCD20.
FIG. 13b shows a FACS analysis of αCD20 expression on 293T cells.

The following experimental methods were used in Examples 1-5 below.
Construct Preparation The cDNAs of the light and heavy chain constant regions of the membrane bound human $IgG_1$ were amplified and inserted downstream of human CMV and EF1α promoters, respectively, of the pBudCE4.1 vector (Invitrogene). (See FIG. 13a.) The light and heavy chain variable regions form the murine anti-CD20 antibody (clone 2H7) were then cloned using PCR amplification and inserted directly upstream of the corresponding constant regions. The resulting construct was designated as pαCD20. (See FIG. 13b.) cDNAs of human Igα and Igβ were also cloned into a pBudCE4.1 vector (Invitrogene) to yield pIgαβ.

The construct encoding HAmu was provided by the laboratory of Dr. Cannon at the University of Southern California (A. H. Lin et al., Hum. Gene. Ther. 12, 323 (2001)). The cDNA for wild-type SIN was obtained from Dr. Strauss's laboratory at Caltech. PCR mutagenesis and assembly were used to generate the mutant SIN as described in Morizono et al., Nature Med. 11, 346 (2005), except that a 10 amino acid residue tag sequence replaced the ZZ domain of protein A, which is located between amino acid 71 and 74 of the E2 glycoprotein of SIN. This version of SIN is designated as SINmu.
Virus Production Lentivirus were generated by transfecting 293T cells using a standard calcium phosphate precipitation technique. 293T cells (~80% confluent) in 6-cm culture dishes were transfected with the appropriate lentiviral vector plasmid (5 µg), together with 2.5 µg each of pαCD20, pIgαβ, and the package vector plasmids (pMDLg/pRRE and pRSV-Rev) (Sandrin et al. Curr. Top. Microbio. Immunol. 281:137 (2003)). The viral supernatants were harvested 48 and 72 hours after transfection and filtered through a 0.45-µm pore size filter.

To prepare high titer lentivirus, the viral supernatants were concentrated using ultracentrifugation (Optima L-80 K preparative ultracentrifuge, Beckman Coulter) for 90 min at 50,000×g. Particles were then resuspended in an appropriate volume of cold PBS.
Cell Line Construction The 293T/CD20 cell line was generated by stable transduction via VSVG-pseudotyped lentivirus. The cDNA of human CD20 was cloned downstream of the human ubiquitin-C promoter in the plasmid FUW (FUGW without GFP; Lois et al. Science 295:868-872 (2002)) to generate FUW-CD20. The lentiviral vector FUW-CD20 was then pseudotyped with VsVg and was used to transduce 293T. The resulting cells were subjected to cell sorting to obtain a uniform population of $CD20^+$ cells designated as 293T/CD20.
Virus-cell Binding Assay Cells (293T/CD20 or 293T, $0.1 \times 10^6$) were incubated with 500 µL of viral supernatant at 4° C. for half an hour and washed with 4 ml of cold PBS. The cells were then stained with the following three antibodies: an anti-human IgG antibody (BD Pharmingen) to stain αCD20, an anti-human CD20 antibody (BD Pharmingen) to stain CD20, and an anti-FPV HA polyclonal antibody (obtained from H.-D. Klenck, Institute of Virology; Philipps-University, Marburg, Germany) to stain HAmu, or an anti-tag antibody (Roche) to stain SINmu. After staining, cells were analyzed by fluorescence-activated cell sorting (FACS.
Targeted Transduction of 293T/CD20 Cells in vitro 293T/CD20 cells ($0.2 \times 10^6$/well) or 293T cells ($0.2 \times 10^6$/well) were plated in a 24-well culture dish, and spin-infected with viral supernatants (0.5 ml/well) at 2,500 rpm, 30° C. for 90 min. using a Beckman Allegra 6R centrifuge. Then the medium was removed and replaced with fresh medium and incubated for a further 3 days at 37° C. with 5% $CO_2$. The percentage of GFP cells was determined by FACS. The transduction titer was measured at the dilution ranges that exhibited a linear response.
Effects of Soluble Antibody and N4Cl on Viral Transduction 293T/CD20 cells ($0.2 \times 10^6$) and 0.5 mL of viral supernatants were incubated for 8 hours in the absence or presence of a gradient dose of anti-human CD20 antibody (BD Pharmingen) or $NH_4Cl$. The medium was replaced with fresh medium and incubated for another 2 days at 37° C. with 5% $CO_2$. FACS analysis was used to quantify transduction efficiency.

Cell-cell Fusion Assay 293T cells ($0.1 \times 10^6$) transiently transfected to express GFP and surface αCD20 and fusion protein (either HAmu or SINmu), and 293T/CD20 cells ($0.1 \times 10^6$) were mixed together, washed twice with normal PBS (pH=7.4), and incubated in 150 μl low pH PBS (pH—5.0) or normal pH PBS (pH=7.4) (as a control) for half an hour at 37° C. with 5% $CO_2$. The cells were then washed extensively and cultured in the regular medium for one day. Cells were visualized by an epifluorescence microscope equipped with a GFP filter set.

Targeted transduction of primary human B cells in vitro

Fresh, un-fractionated human peripheral blood mononuclear cells (PBMCs) ($2 \times 10^6$) (AllCells, LLC) were incubated with concentrated virus with total transduction units (TU) of $10 \times 10^6$ (based on the titer on 293T/CD20 cells). LPS (50 μg/mL) was then added for B cells to survive and grow. After two days, cells were harvested and washed in PBS. B cell population was determined by FACS staining using anti-human CD20 and CD19 antibodies. Targeting transduction was quantified by gating on the different populations of cells and measuring their GFP expression.

Targeted Transduction of Primary Human B Cells in vivo $RAG^{-1-}{}_{\gamma c}{}^{-1-}$ female mice (Taconic) of 6-8 weeks old were given 360 rads whole body irradiation. On the following day, $100 \times 10^6$ fresh human PBMCs (AllCells, LLC) were transferred by tail vein injection into each mouse. After six hours, concentrated viruses ($100 \times 10^6$ TU/mouse) or PBS (as control) were administered into these mice via the tail vein. Two days later, whole blood was collected from these mice via heart puncture and the cells were stained for human CD3 and CD20 and then analyzed by FACS for CD3, CD20 and GFP expression. The mice were maintained on the mixed antibiotic sulfinethoxazole and trimethoprim oral suspension (Hi-Tech Pharmacal) in a sterile environment in the California Institute of Technology animal facility in accordance with institute regulations.

Example 1

Targeted Cell Transduction Utilizing Retroviral Vectors FUGW/αCD20+HAmu and FUGW/αCD20+SINmu One antibody chosen to serve as the basis of an affinity molecule, according to some embodiments of the invention, is the anti-CD20 antibody (αCD20), a version of which is currently being used in the treatment of B-cell lymphomas. Physiologically, CD20 is expressed at the pre-B-cell stage of development and throughout B-cell maturation; hematopoietic stem cells do not express CD20. When B-cells mature into plasma cells, expression of CD20 is diminished. Thus, CD 20 represents an ideal target for therapy of, for example, B-cell lymphomas and leukemia. A construct that encodes a mouse/human chimeric anti-CD20 antibody with the human membrane-bound IgG constant region (pαCD20) was generated as described above. Genes encoding human Igα and 10, the two associated proteins that are required for surface expression of antibodies, were cloned into a construct designated pIgαβ (FIG. 1).

Figure 14:
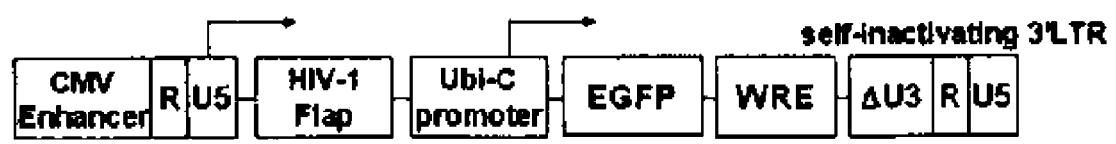
FIG. 14 illustrates schematically the lentiviral vector FUGW.
Figure 15:
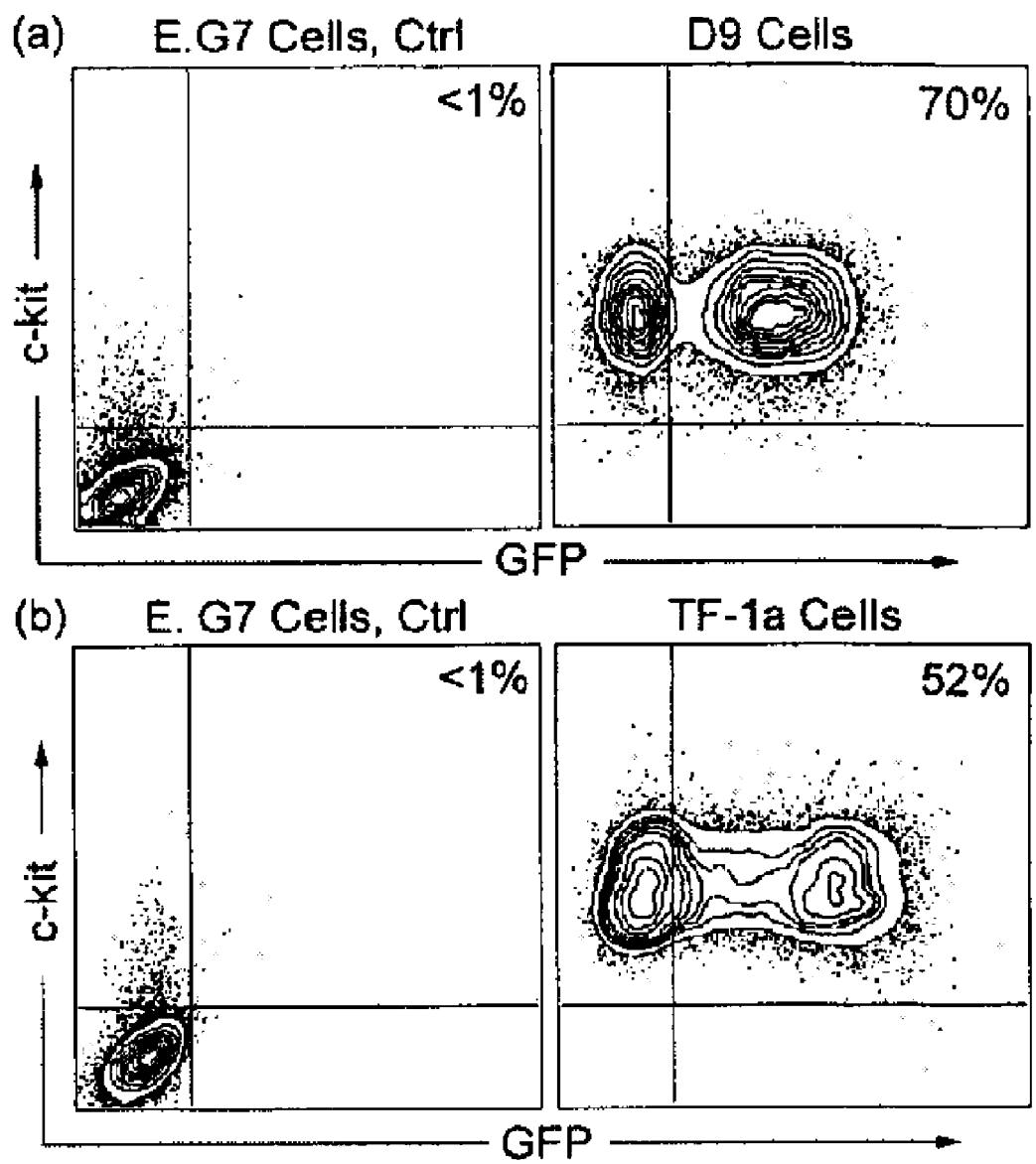
FIG. 15a illustrates the results of infection of c-kit-expressing D9 cells with FUGW/mSCF+SINmu, E.G7 cells used as controls.
FIG. 15b illustrates the results of infection of c-kit-expressing TF-1a cells with FUGW/mSCF+SINmu, E.G7 cells used as controls.
Figure 16:
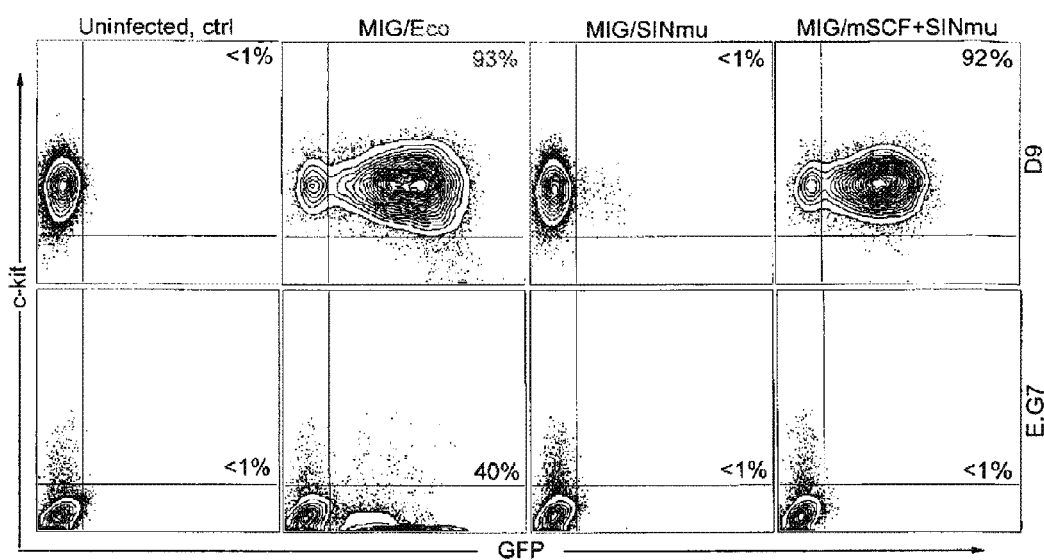
FIG. 16 illustrates the results of targeting retroviruses bearing SCF and SINmu to c-kit-expressing cells, E.G7 used as controls.

The production of lentiviruses enveloped with both anti-CD20 antibody and candidate fusion molecules (FMs) was achieved by co-transfection of 293T cells with the lentiviral vector FUGW (Lois et al. *Science* 295:868-872 (2002)), plasmids encoding viral gag, pol, and rev genes, pαCD20, pIgαβ and pFM (the plasmid encoding a FM, either HAmu or SINmu), using a standard calcium phosphate precipitation method. FUGW is a self-inactivating and replication-incompetent lentiviral vector which carries the human ubiquitin-C promoter driving the GFP reporter gene (C. Lois, E. J. Hong, S. Pease, E. J. Brown, D. Baltimore, Science 295, 868 (2002)). (See FIG. 14.) As a control, the envelope glycoprotein derived from vesicular stomatitis virus (VSVG) was used as recognition and fusion protein.

FACS analysis of the transfected cells showed that virtually all expressed some level of GFP as an indicator of the presence of the viral vector (FIGS. 3B and 3D, upper panels). Some 30% of GFP-positive cells co-expressed HAmu and αCD20 on the cell surface (FIG. 3B, lower panel). A slightly smaller percentage (~20%) of the 293T cells exhibited co-expression of GFP, SINmu, and αCD20 (FIG. 3D). The resultant viruses from these transfected production cells were designated FUGW/αCD20+HAmu and FUGW/αCD20+SINmu.

Figure 4:
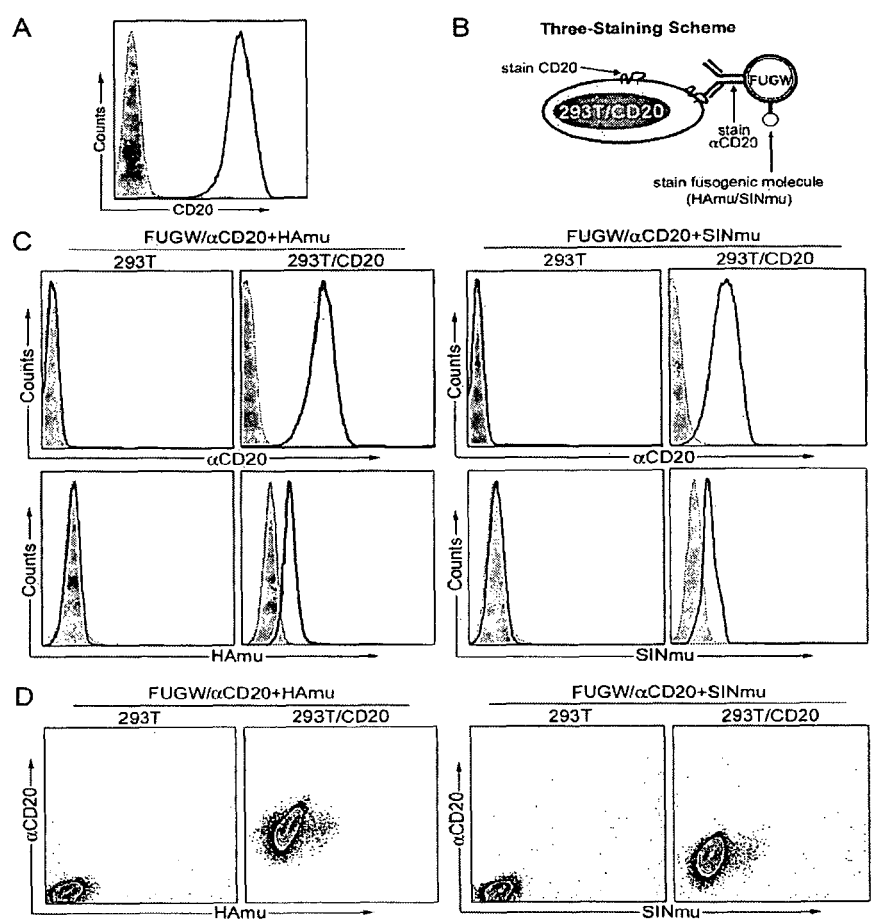
FIG. 4A illustrates FACS analysis of target cell line 293T/CD20. CD20 expression was detected using anti-CD20 antibody. The solid line shows expression of CD20 in 293T/CD20; the shaded line shows CD20 expression in 293T cells (as a control).
FIG. 4B is a schematic representation of a three-staining scheme used for analyzing virus-cell binding. Three stains were used to detect the presence of CD20, αCD20 and the fusogenic molecule (HAmu or SINmu), respectively.
FIG. 4C, left panel, illustrates FACS plots of 293T/CD20 cells incubated with FUGW/αCD20+HAmu. The binding of virus to 293T/CD20 cells was probed with antibody against αCD20 (anti-IgG) and HAmu. The solid line indicates analysis on 293T/CD20; the shaded line shows analysis on 293T (as a control). The right panel of FIG. 4C shows FACS plots of 293T/CD20 cells incubated with FUGW/αCD20+SINmu. The binding of virus to 293T/CD20 cells was detected by antibody against αCD20 and SINmu. The solid line shows analysis on 293T/CD20; the shaded line shows analysis on 293T (as a control).
FIG. 4D illustrates co-display of antibody and fusogenic protein through a density plot correlating the presence of the two proteins.

To examine whether αCD20 and the FM were incorporated in the same virion, a virus-cell binding assay was performed. As a target, a 293T cell line was made stably expressing the CD20 protein antigen, as described above (293T/CD20, FIG. 4A). The parental cell line 293T served as a negative control. The viral supernatants were incubated with the target cells at 4° C. for half an hour. The resultant binding was assayed via a three-staining scheme (FIG. 4B). FACS analysis showed that recombinant lentivirus bearing αCD20 was in fact able to bind to CD20 expressing 293T cells (FIG. 4C, upper panels). The control of 293T cells with no CD20 expression displayed no detectable αCD20, showing that the virus binding to cells must be due to a specific interaction between the cell surface CD20 antigen and the viral surface αCD20 molecule. In another control, the virus bearing only FM exhibited no ability to bind both cells, indicating that the HAmu and SINmu did lack the capacity for cell binding. FACS analysis also showed that the virus bound to the 293T/CD20 cell surface displayed the FMs (FIG. 4C, lower panels), suggesting that both αCD20 and FM were incorporated on the same virion, which was further confirmed by FACS plots of αCD20 versus FM (FIG. 4D). In addition to co-display, these results indicate that the presence of the FM does not affect the αCD20 binding to CD20.

Figure 17:
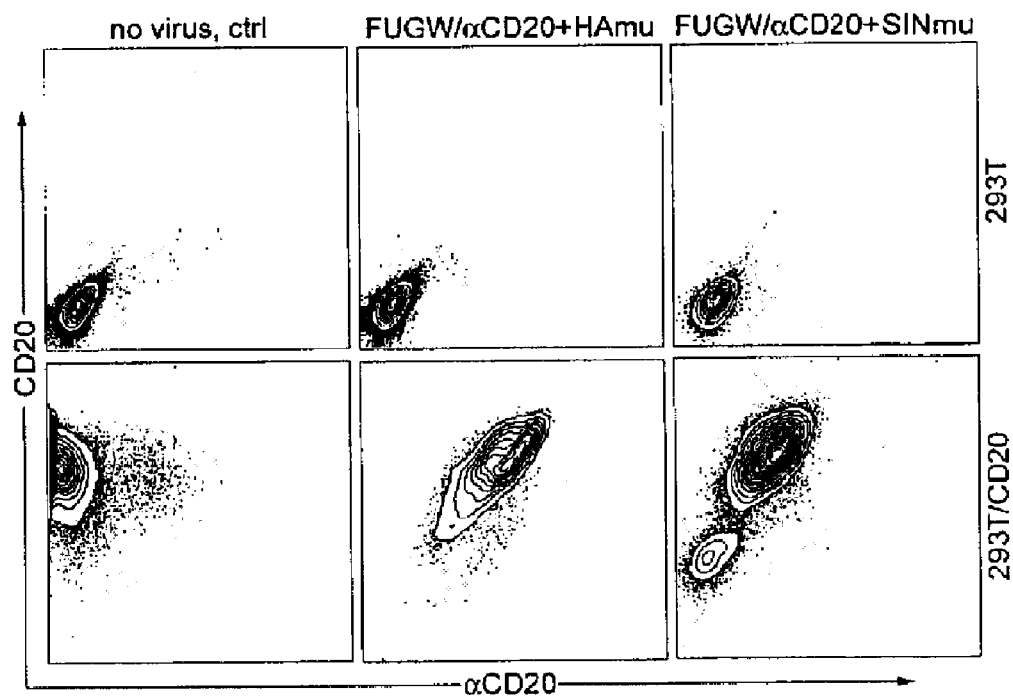
FIG. 17 illustrates FACS analysis of lentiviral particles bearing αCD20 to bind 293T/CD20 cells.

To confirm that αCD20 was functionally displayed on the lentiviral surface, a virus-cell binding assay was performed. 293T cells were engineered to over-express CD20. The human CD20 was cloned and its expression on 293T cells was confirmed by FACS staining. 293T cells stably expressing CD20 antigen were sorted out as target cells (designated as 293T/CD20). Viral supernatants were incubated with 293T/CD20 cells at 4° C. for 1 hr; 293T were included as controls. Binding activity was measured by FACS staining using the antibody against the constant region of αCD20 (human IgG C region); cells were also co-stained with the antibody against the surface antigen CD20. As shown in FIG. 17, our binding assay revealed that lentiviruses displaying αCD20 (FUGW/αCD20+HAmu and FUGW/αCD20+SINmu) were able to specifically bin to $CD20^+$ cells, suggesting αCD20 was indeed functionally incorporated onto the viral surface. FACS plots also indicated the down-regulation of CD20 on the 293T surface upon virus binding.

Example 2

Figure 5:
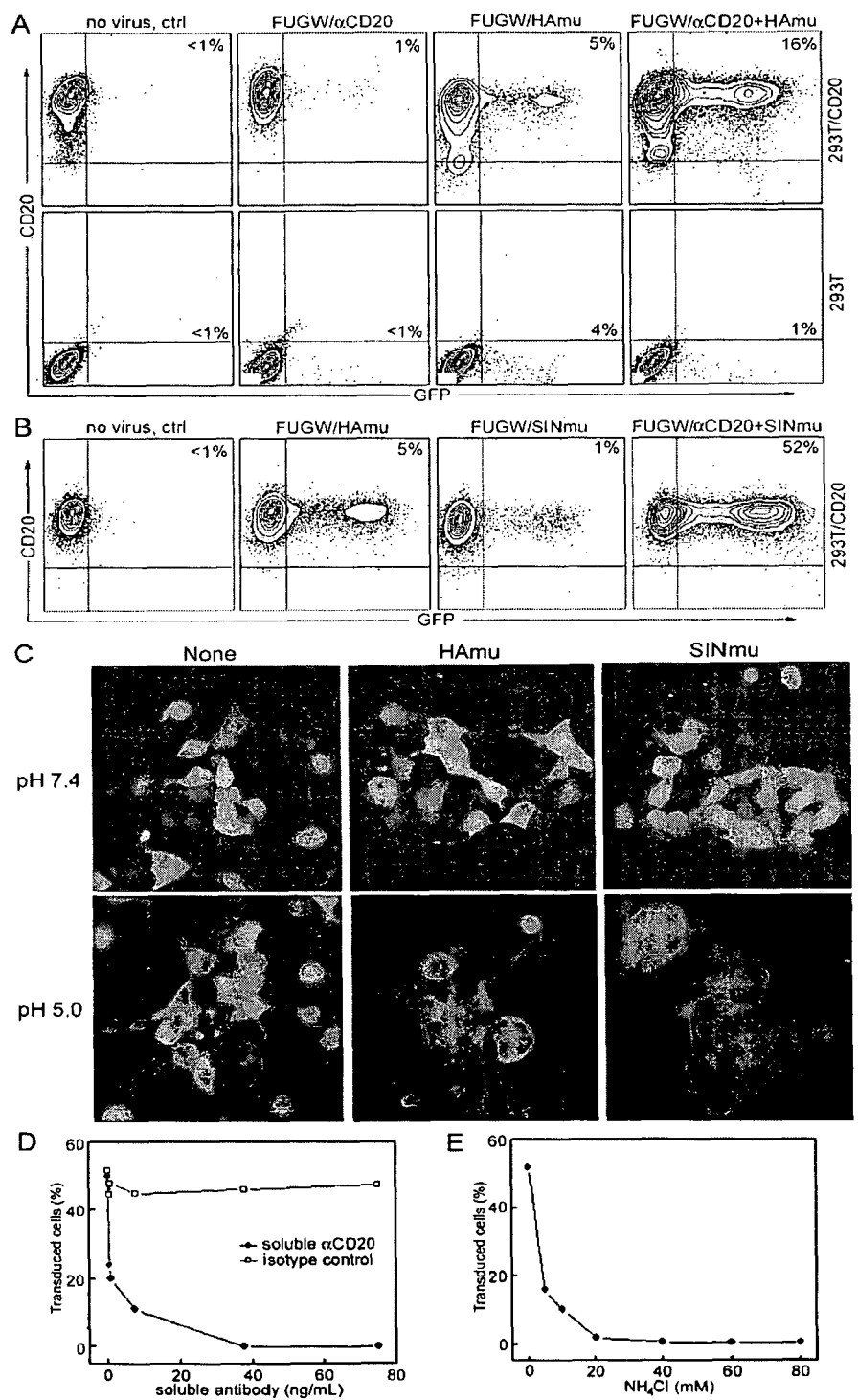
FIG. 5A shows density plots illustrating targeting of recombinant lentivirus bearing both antibody and fusion protein to 293T/CD20 cells in vitro. 293T/CD20 cells ($2 \times 10^5$) were transduced with 500 μL fresh unconcentrated FUGW/αCD20 (no HAmu), FUGW/HAmu (no αCD20), or FUGW/αCD20+HAmu. 293T cells that did not express CD20 were included as controls. The resulting GFP expression was analyzed by FACS. The specific transduction titer for FUGW/αCD20+HAmu was estimated to be $\sim 1 \times 10^5$ TU/mL.
FIG. 5B illustrates results from a similar transduction experiment to that shown in FIG. 5A, but performed using unconcentrated FUGW/SINmu (no αCD20) or FUGW/αCD20+SINmu. For comparison of targeting specificity, cells were also transduced with FUGW/HAmu. The specific transduction titer for FUGW/αCD20+SINmu was estimated to be $\sim 1 \times 10^6$ TU/mL.
FIG. 5C illustrates evidence of pH-dependent fusion of HAmu and SINmu by a cell-cell fusion assay. 293T cells ($0.1 \times 10^6$) transiently transfected to express GFP and surface αCD20 and fusion protein (either HAmu or SINmu), and 293T/CD20 cells were mixed together, washed once with normal PBS (pH=7.4), and incubated in low pH PBS (pH=5.0) or normal pH PBS (as a control) for half an hour at 37° C. The cells were then washed and cultured in the regular medium for one day. Cells were visualized by epifluorescence microscope equipped with a GFP filter set.
FIG. 5D illustrates the effect of addition of soluble αCD20 on transduction with viral particles displaying αCD20 and a fusogenic protein. αCD20 was added into viral supernatants during transduction for 8 hours. Then the supernatants were replaced with fresh medium. The cells were analyzed for GFP expression after two days. Isotype-matched antibody was used as a control.
FIG. 5E illustrates the pH dependence of transduction based on the effect of addition of $NH_4Cl$ (instead of soluble αCD20).

Transduction of CD20-expressing Target Cells and 293T Cells Utilizing the Retroviral Vector FUGW/αCD20+HAmu and FUGW/αCD20+SINmu Next, the efficacy of a αCD20-bearing virus in transferring genes into cells expressing CD20 in a cell-specific manner was tested. GFP expression was used to measure the transduction efficiency. The supernatants containing virus bearing various surface proteins were incubated with CD20-expressing target cells and 293T cells served as a control. Four days post-transduction, the efficiency of targeting was analyzed by FACS. FIG. 5A (rightmost panel) shows that FUGW/αCD20+HAmu viral particles could specifically transduce 16% of 293T/CD20 cells. Panels to the left show that transduction required the presence on the virions of HAmu, but there was some background transduction with virions lacking αCD20, likely due to residual weak binding of HAmu to its ligand, sialic acid. The titer for FUGW/αCD20+HAmu (fresh viral supernatant, no concentration) was estimated to be $\sim 1 \times 10^5$ transduction units (TU)/mL. The titer was determined by the percentage of GFP cells in the dilution ranges that showed a linear response. The 293T cells showed a small background infection level but no specific transduction by FUGW/αCD20+Hamu (FIG. 5A, lower panels).

When SINmu was used as the fusion protein, substantial enhancement of specific transduction was observed (52%, FIG. 5B). The titer for FUGW/αCD20+SINmu was estimated to be $\sim 1 \times 10^6$ TU/mL. Also, a much lower transduction was detected in the absence of the binding protein ($\sim 1\%$). Thus the data in FIG. 5B shows that SINmu is a preferred fusion protein to partner with αCD20 for targeting the virus. When the transduction was monitored at various time points using FACS, it was found that SINmu-containing virions exhibited faster transduction kinetics than those with HAmu. Both FUGW/αCD20+HAmu and FUGW/αCD20+SINmu could be concentrated by ultracentrifugation with a >90% recovery rate, which is important for in vivo applications.

To assess whether αCD20 and the fusion protein (HAmu or SINmu) had to be incorporated into the same viral particle, and therefore functioned in cis to mediate transduction, Virus generated from FUGW/αCD20 was mixed with virus generated from FUGW/HAmu or FUGW/SINmu, each displaying only one protein, and their transduction of 293T/CD20 cells was tested. This procedure did not result in specific transduction, indicating that the specific transduction conferred by the engineered recombinant viruses requires that the two proteins be displayed on the same viral particle.

Thus, two distinct proteins can contribute to the binding and fusion events of engineered lentiviruses for targeted transduction. To further confirm that the specificity observed was a consequence of interaction between αCD20 and CD20, 293T/CD20 cells were transduced in the presence of anti-CD20 blocking antibody. As expected, a dramatic decrease of infectivity was detected for both FUGW/αCD20+HAmu and FUGW/αCD20+SINmu virus (FIG. 5D), indicating that antibody-antigen binding facilitates targeted transduction.

To examine the requirement for a low pH compartment to allow the recombinant lentivirus to penetrate into cells, both FUGW/αCD20+HAmu and FUGW/αCD20+SINmu virus was incubated with 293T/CD20 cells in the absence or presence of ammonium chloride ($NH_4Cl$), which neutralizes acidic endosomal compartments. Addition of $NH_4Cl$ to cells completely abolished transduction by either FUGW/αCD20+HAmu virus (not shown) or FUGW/αCD20+SINmu (FIG. 5E). These results are consistent with the low pH requirement of hemagglutinin and Sindbis virus glycoprotein to trigger membrane fusion.

More direct evidence for pH dependent fusion was provided by a cell-cell fusion assay. 293T cells expressing GFP and surface αCD20 and FM were incubated with 293T/CD20 cells in a low-pH buffer for half an hour, followed by culturing in regular medium. Both HAmu and SINmu induced cell-cell fusion by forming multi-nucleated polykaryons (FIG. 5C). The interaction between αCD20 and CD20 dramatically enhances the probability of fusion, because a similar experiment with cells that lacked αCD20 and CD20 yielded a much lower level of fusion. The αCD20/CD20 interaction brings the cell membranes into close approximation, facilitating the action of the fusion protein.

Example 3

Transduction of Primary Human B-Lymphoid Cells Using the Retroviral Vector FUGW/αCD20+SINmu Having established the ability of the system to mediate CD20-specific transduction of artificially created cell lines, the specific transduction of primary human B-lymphoid cells, cells that naturally carry the CD20 antigen, was investigated. Fresh, unfractionated human peripheral blood mononuclear cells (PBMCs) were transduced with FUGW/αCD20+SINmu and then stimulated with lipopolysaccharide (LPS) to expand the B cell population. Four days later, the cells were stained for CD19 (a B cell marker), CD20 and GFP expression (FIG. 6A). Over 35% of cells were $CD20^+$ B cells under the described culture condition. The majority of them were $GFP^+$. On the contrary, virtually no $GFP^+$ cells were detected among $CD20^-$ non-B cells, confirming that the transduction was strictly dependent on CD20 expression. In another control experiment, fresh PBMCs were transduced with FUGW/αCD20+SINmu followed by stimulation with phorbol-12-myristate-13-acetate (PMA) and ionomycin to expand T cells. FACS analysis of these T cells showed no expression of GFP (FIG. 7), confirming transduction specificity.

Example 4

Demonstration of Transduction Utilizing Lentiviral Vectors CCMV/αCD20+SINmu and CPGK/αCD20+SINmu To demonstrate that the targeting method is not limited to the lentiviral vector FUGW, two additional lentiviral vectors with different promoter configurations were evaluated. Kohn et al. have incorporated the immunoglobulin heavy chain enhancer (Eμ) with associated matrix attachment regions into lentivectors carrying either the human cytomegalovirus (CMV) promoter (CCMV) or the murine phosphoglycerate kinase promoter (CPGK) (C. Lutzko et al. *J. Virol.* 77, 7341-51 (2003)). These two lentiviral vectors were then adapted into the system and recombinant lentiviruses CCMV/αCD20+SINmu and CPGK/αCD20+SINmu were prepared. Transduction of PBMC-derived B cells with these viral supernatants exhibited results similar to those observed previously with FUGW (FIG. 6A). Stable integration of the GFP-transgene was detected by genomic PCR amplification (FIG. 6B).

Example 5

Testing of in vivo Efficacy of Lentiviral Vectors in Mediating Specific Transduction Next, the efficacy of the system in mediating specific transduction in vivo was tested. For this purpose, a human PBMC xenografted mouse model was used. Fresh human PBMCs ($100\times 10^6$/mouse) were transferred into irradiated immunodeficient $RAG2^{-/-}\gamma_c^{-/-}$ mice through a tail vein injection. Engineered lentiviruses bearing αCD20 and SINmu were administered through the tail vein 6 hours after human cell transfer. After 2 days, whole blood from these mice was collected and the cells were analyzed for surface antigens and GFP expression.

Figure 6:
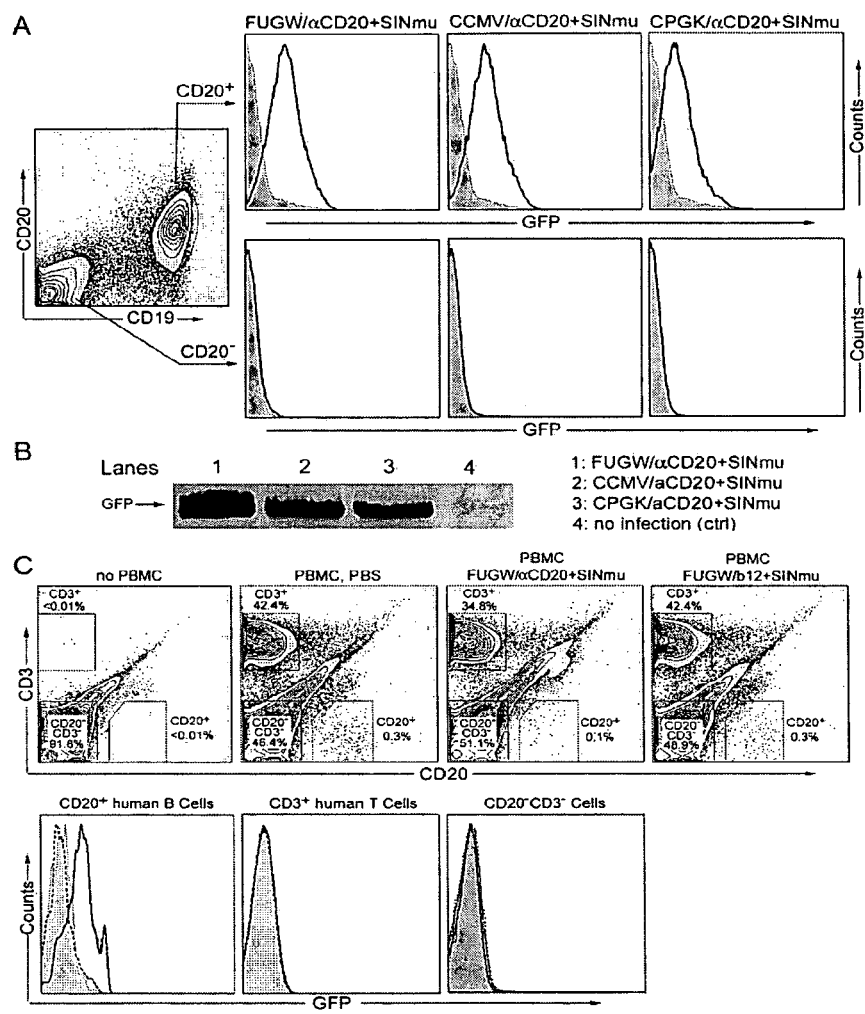
FIG. 6 shows the targeting of $CD20^+$ human primary B cells in vitro and in vivo using engineered lentivirus.
Figure 7:
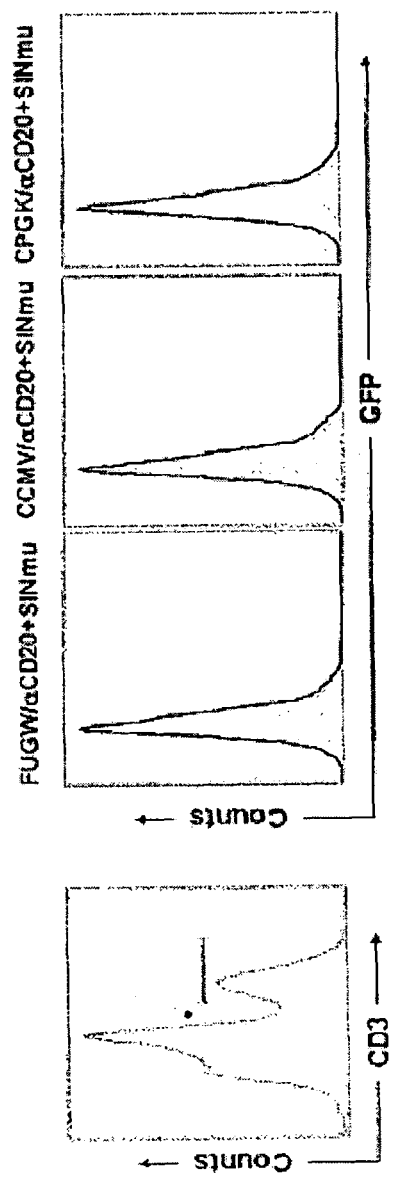
FIG. 7 illustrates expression of a gene of interest using virus prepared from three different viral constructs. Fresh, unfractionated human PBMCs ($2 \times 10^6$) were transduced by co-culturing with concentrated FUGW/αCD20+SINmu, CCMV/αCD20+SINmu or CPGK/αCD20+SINmu ($10 \times 10^6$ TU). PMA (50 ng/mL) and ionomycin (500 ng/mL) was added into the culture media to enhance T cells survival and growth. After two days, the T cell population was identified by co-staining of human CD3. The solid line shows analysis on transduced cells; the shaded line illustrates analysis on cells without transduction (as a control).

Approximately 30-40% of the cells recovered from the mice were human T cells (CD3$^+$) and 0.1~0.3% were CD20$^+$ human B cells. Three populations were analyzed for GFP expression: CD20$^+$, CD3$^+$, and CD20$^-$CD3$^-$. None of the cells harvested from mice injected with virus bearing a control antibody and SINmu (FUGW/b12+SINmu) showed evidence of GFP expression in any of the three populations (FIG. 6C). In contrast, GFP expression was observed in at least 40% of the CD20$^+$ cells isolated from mice injected with FUGW/αCD20+SINmu while no transduction was detected in the other two populations.

This demonstration of targeting efficient gene delivery vehicles strictly to the desired cell types in vivo allows for lentivirus-mediated gene therapy and alleviates concerns of off-target effects. Possibly the most important implication of the work is that gene therapy can now be carried out as an inexpensive procedure, and thus a viable consideration even in the less-developed world.

Example 6

Infection of Dendritic Cells Expressing the DEC-205 Receptor by Recombinant Lentiviral Vector FUGW/αmDEC-205+SINmu To evaluate the use of affinity molecules such as surface antibodies to target lentiviral vectors, membrane-bound antibody against the mouse DEC-205 receptor (designated as αmDEC-205) was prepared as described above for the anti-CD20 antibody. αmDEC-205 is an endocytic receptor abundantly expressed on dendritic cells (DCs).

Figure 8:
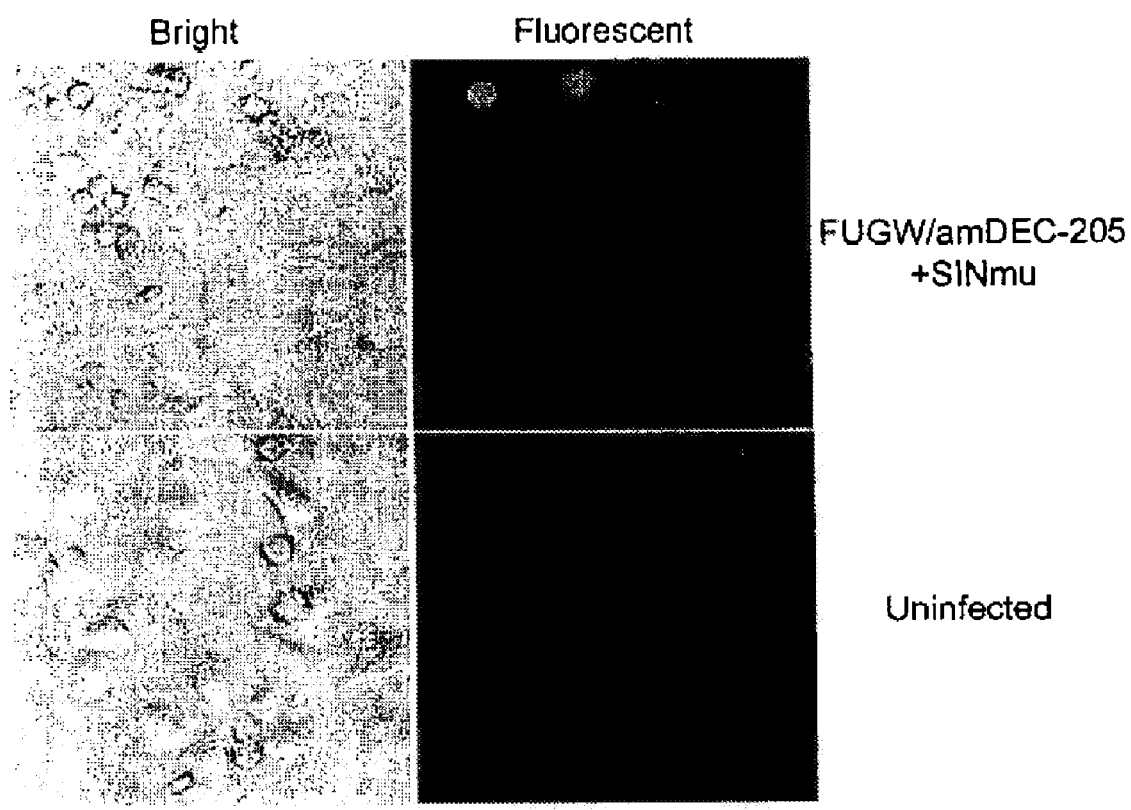
FIG. 8 illustrates a fluorescent microscopy examination of the infection of dendritic cells using FUGW/αmDEC205+SINmu.
Figure 9:
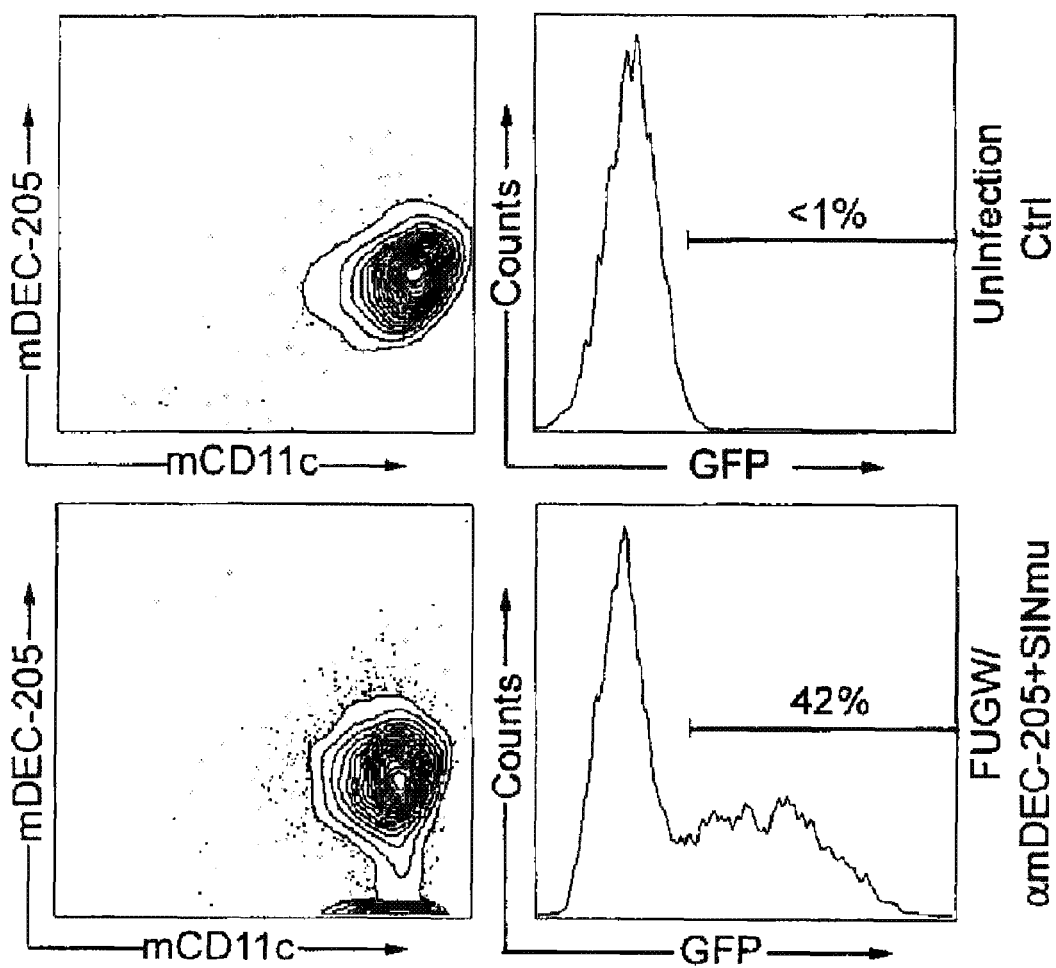
FIG. 9 illustrates a FACS analysis of DCs infected by FUGW/αmDEC-205+SINmu. Uninfection included as controls.

A protocol was adopted to generate mouse DCs from progenitors grown in bone marrow cultures (Yang L and Baltimore D. *Proc. Natl. Acad. Sci. USA* 102:4518 (2005)). Bone marrow cells were harvested from mice and cultured in vitro in the presence of granulocyte-macrophage colony stimulating factor (GM-CSF). On day 10 cells were collected and it was confirmed that 70% of the cells expressed DEC-205. Virus-cell binding assay showed that recombinant FUGW/αmDEC-205+SINmu could bind to DEC-205 positive cells. When the DCs complexed with viruses were analyzed, significant downregulation of DEC-205 was observed. Infection of these cells with viral supernatants followed a very similar pattern to that seen previously with αCD-20. When DCs were gated on (mCD11c high), FUGW/αmDEC-205+SINmu exhibited high infection efficiency (42%) whereas FUGW/αmDEC-205 and FUGW/SINmu exhibited virtually no infection. (See FIGS. 8 and 9.) Downregulation of DEC-205 was observed on DCs infected with viruses bearing αmDEC-205. These results also showed that recombinant retroviruses such as described above can efficiently infect primary cells.

Example 7

Use of a Single Chain Membrane-bound Antibody (Anti-CD 20) with a Recombinant Lentivirus to Target CD20-expressing Cells A single chain membrane-bound form of antibody (scAbm) was developed as an affinity molecule target recombinant lentivirus. scAbms are typically designed to have heavy chain and light chain variable domains linked by a flexible peptide linker. They also carry a signal peptide at their N terminus and a transmembrane domain at their C terminus for anchoring to the cell surface. A slightly different version of scAbm devised is designated as scαCD20. (See FIG. 10a) This scAbm was composed of heavy chain and light chain variable domains of anti-CD20 antibody linked by (GGGGSGGGS)$_2$ (SEQ ID NO. 1) peptide, and a dimerization region including the hinge CH2-CH3 domain of human IgG1, and the transmembrane domain and the cytoplasmic tail of the human HLA-A2 to display this chimeric protein on the cell surface.

Figure 10:
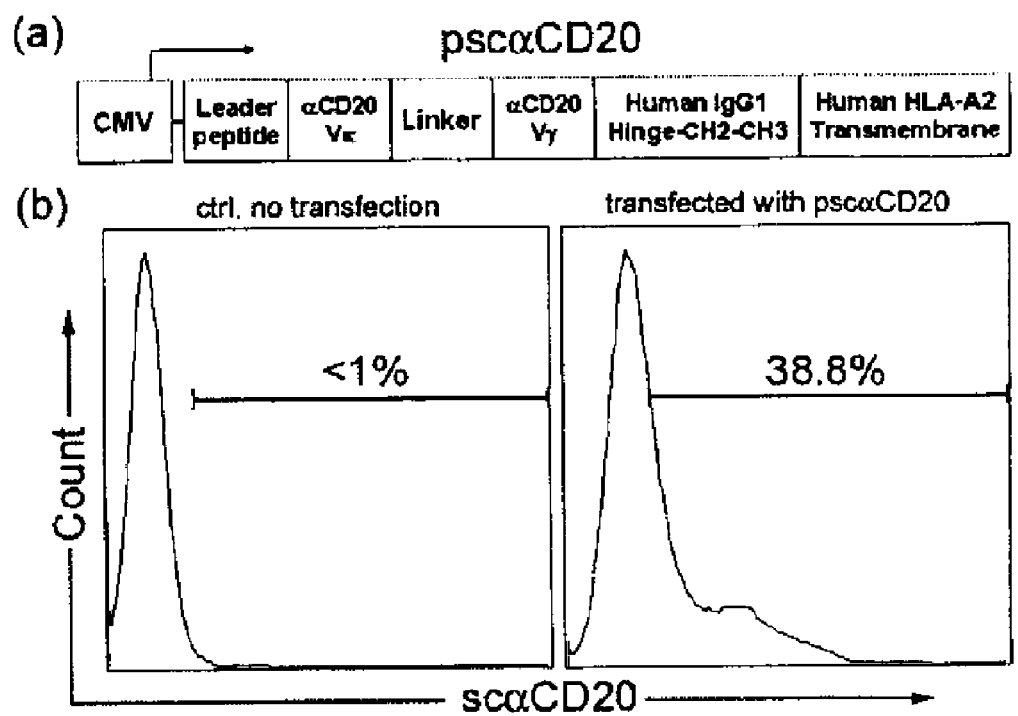
FIG. 10a shows a construct for expression of single chain antibody (scαCD20).
FIG. 10b shows a FACS analysis of scαCD20 expression on 293T cells.

The ability of scαCD20 to be expressed on the cell surface was examined by FACS analysis. As shown in FIG. 10b, transfection of 293T cells with the expression vector of pscαCD20 resulted in higher levels of surface antibody expression, when compared to those versions of scAbms without a dimerization domain in the literature (e.g., de Ines, C. et al. *J. Immunol.* 163, 3948-3956 (1999)). This may be partially due to the inclusion of the disulfide-linked dimerization domain, which improves stability of scAbm on the surface.

Virus-cell binding assay was employed to examine whether pscαCD20 retained its binding activity. The supernatant of scαCD20-bearing lentiviruses (designated as FUGW/scαCD20+SINmu) was incubated with 293T/CD20 cells and the resulting virus-cell complexes were analyzed by FACS. It was found that FUGW/scαCD20+SINmu viruses were able to bind to CD20-expressing 293T cells, indicating that scαCD20 on the viral surface was active.

Figure 11:
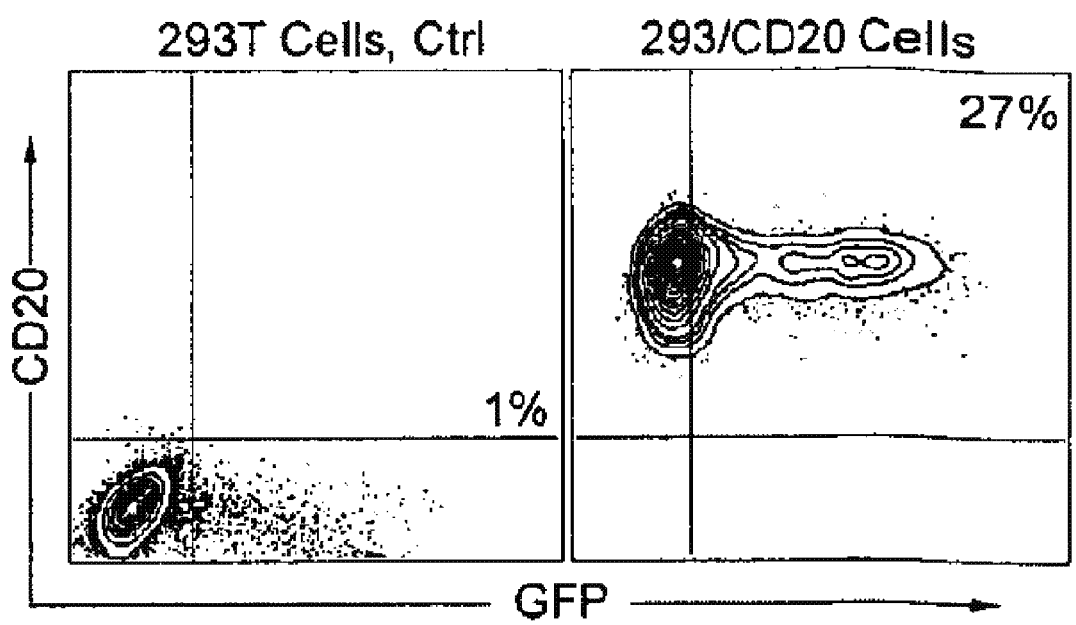
FIG. 11 shows a FACS analysis of 293T/CD20 cells transduced with FUGW/scαCD20+SINmu.

The ability of FUGW/scαCD20+SINmu to specifically transduce CD20$^+$ cells was next investigated. As shown in FIG. 11, lentiviruses carrying scαCD20 can transduce 293T/CD20 cells expressing CD20. The titer was estimated to be around $5 \times 10^5$ IU/mL. Lentiviruses incorporating a single chain antibody had a somewhat lower titer than those incorporating the natural form of antibody, possibly because of the ability of the natural form of the antibody to induce endocytosis. Nevertheless, these results demonstrated that scAbm can be used to generate lentiviruses capable of transducing cells expressing cognate receptors.

Example 8

Specific Infection of Cells Expressing Surface-bound Anti-CD20 Antibodies Using an Engineered Recombinant Lentivirus Carrying CD20 and Fusion Proteins Experiments to address (1) whether surface proteins other than antibodies can be used to target lentiviral vectors, and (2) whether surface receptors other than CD20 could be targeted for cell-specific transduction were performed.

Figure 12:
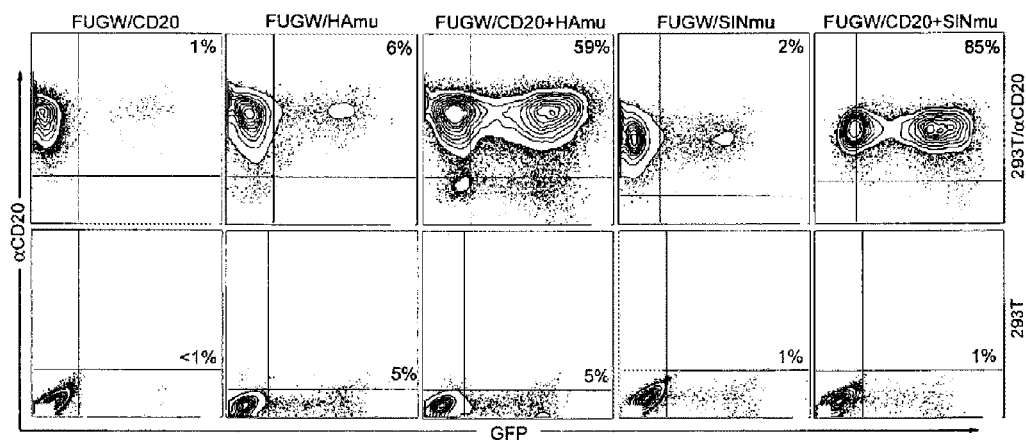
FIG. 12 illustrates targeting of lentiviruses bearing CD20 and fusion protein to 293T/αCD20 cells.

The use of CD20 to target cells expressing αCD20 was investigated. Unlike CD20, which is a 4-transmembrane protein, membrane-bound IgG$_1$ has a C-terminal transmembrane and cytoplasmic portions that anchor the molecule in the plasma membrane. Physiologically the cytoplasmic domains can mediate internalization of antigen-immunoglobulin complexes (Nussenzweig, M. C. *Curr. Biol.* 7, R355-357 (1997)). 293T cells were stably generated expressing membrane-bound αCD20, designated herein as 293T/αCD20. Harnessing the nature of the budding mechanism, recombinant lentiviruses carrying CD20 and HAmu/SINmu (designated as FUGW/CD20+HAmu and FUGW/CD20+SINmu, respectively) were prepared. Infectivity of lentiviruses bearing CD20 was measured by transducing 293T/αCD20 and quantifying GFP expression. As shown in FIG. 12, FUGW/CD20+ HAmu virus can specifically transduce 293T cells expressing αCD20. The titer was estimated to be about $1.2 \times 10^6$ IU/mL. This data indicates that the membrane-bound antibody can act as a viral receptor to mediate entry of lentiviruses carrying the cognate antigen.

Therefore, it was demonstrated that transmembrane proteins such as CD20 can be incorporated into the viral surface to target the lentiviral vectors, expanding the pool of proteins that can be exploited for targeting strategies. These results also show to one of ordinary skill in the art that many different types of cell surface receptors can be utilized as affinity molecules to mediate the targeted entry.

Example 9

Specific Infection of Cells Expressing c-kit Using an Engineered Recombinant Lentivirus Co-displaying the Membrane-bound Form of Stem Cell Factor (SCF) and Fusion Proteins It was investigated whether other surface receptor-ligand interactions could be exploited to achieve targeting. Stem cell factor (SCF) interacts with c-kit, a protein tyrosine kinase receptor on cell surfaces, to modulate hemopoiesis. (Shimizu, Y. J. et al. *J Immunol.* 156, 3443-34491996)). It was found that engagement of SCF with c-kit led to rapid internalization of c-kit via the endosomal pathway (Jahn, T. et al. *Oncogene* 21, 4508-4520 (2002)). Casimir et al. showed that membrane-bound human SCF could be incorporated into ecotropic retroviruses and found that the resulting viruses were able to specifically transduce c-kit-expressing human cells (Chandrashekran, A., et al. *Blood* 104, 2697-2703 (2004)). Original ecotropic viruses do not infect human cells because the envelope protein Eco cannot recognize mCAT expressed on the human cell surface (the mCAT derived from rodent cells is the viral receptor for Eco; Coffin, J. M. et al. (1997). Retroviruses (New York, Cold Spring Harbor Laboratory Press)). The ability of HAmu and SINmu to coordinate with SCF to target recombinant lentiviruses and retroviruses was evaluated.

The membrane-bound form of human SCF (designated as hSCF) was cloned from the s1/s14 hSCF220 stromal cell line (obtained from ATCC). To construct the membrane-bound form of mouse SCF (designated as mSCF), the cDNA for secreted mouse SCF was linked with the transmembrane portion of hSCF. It was found that both hSCF and mSCF could be stably displayed on the surface of lentiviruses. When HAmu and hSCF were engineered into recombinant lentiviruses (FUGW/hSCF+HAmu), the viruses, failed to infect TF-1a cells expressing human c-kit. Similarly, FUGW/mSCF+HAmu could not infect D9 cells expressing mouse SCF receptor. On the other hand, when SINmu was used, FUGW/mSCF+SINmu and FUGW/mSCF+SINmu were able to specifically infect c-kit positive cells TF-1a and D9 respectively. (See FIGS. 15*a* and *b*.) Their titers were estimated to be about $1.5\times10^6$ IU/mL and $4\times10^6$ IU/ml, respectively. These results indicate the appropriate coordination between fusion and recognition protein is an important factor for the recombinant virus to be infectious.

When retroviruses displaying mSCF and SINmu were displayed to infect D9 cells, extremely high infectivity (93%) was obtained. (See FIG. 16.) Retroviruses carrying only mSCF or SINmu exhibited virtually no infection of D9 cells. The infectivity was as high as what Eco pseudotyped viruses could achieve. This indicates that receptor ligand pairs can be used to target retroviruses to particular target cells.

What is claimed is:

1. A method of delivering a polynucleotide encoding an antigen of interest to a dendritic cell, the method comprising:

infecting the dendritic cell with a recombinant lentivirus, wherein the recombinant lentivirus comprises:

(i) the polynucleotide encoding the antigen of interest and wherein the polynucleotide is operably linked to an expression control sequence, and wherein the polynucleotide further comprises an R sequence and an U5 sequence from a 5' lentiviral long terminal repeat (LTR), and a self-inactivating lentiviral 3' LTR, and (ii) a viral envelope comprising a fusogenic molecule which is a Sindbis virus E1 glycoprotein, and a cell-specific binding determinant which is an anti-DEC-205 antibody that (a) targets dendritic cells, (b) is separate from the fusogenic molecule, and (c) is incorporated into the envelope of the recombinant lentivirus.

2. The method of claim 1, wherein the antibody comprises the light and the heavy constant chain regions of human IgG1.

3. The method of claim 1, wherein the cell-specific binding determinant further comprises immunoglobulin alpha and immunoglobulin beta.

4. The method of claim 1, wherein the antibody is a single chain antibody.

5. The method of claim 4, wherein the single chain antibody is fused with a transmembrane domain from another protein.

6. The method of claim 1, wherein the R sequence and the U5 sequence are from HIV.

7. The method of claim 1 wherein the self-inactivating 3' LTR comprises a U3 element with a deletion of its enhancer sequence.

8. The method of claim 7, wherein the self-inactivating 3' LTR is a modified HIV 3' LTR.

9. The method of claim 1, wherein the recombinant lentivirus is pseudotyped.

10. The method of claim 1, wherein the antigen of interest is a tumor antigen.

11. The method of claim 1, wherein the envelope comprises a Sindbis virus E2 glycoprotein.

12. The method of claim 1, wherein the recombinant lentivirus further comprises a stimulatory molecule.

\* \* \* \* \*